(12) United States Patent
Rieger

(10) Patent No.: US 11,737,886 B2
(45) Date of Patent: Aug. 29, 2023

(54) PLACEHOLDER FOR SPINAL SURGERY

(71) Applicant: I-PEGO GMBH, Frechen, DE (US)

(72) Inventor: Bernhard Rieger, Rostock (DE)

(73) Assignee: I-Pego GmbH, Frechen (DE)

( * ) Notice: Subject to any disclaimer, the term of this patent is extended or adjusted under 35 U.S.C. 154(b) by 22 days.

(21) Appl. No.: 17/051,619

(22) PCT Filed: Apr. 27, 2019

(86) PCT No.: PCT/EP2019/060834
§ 371 (c)(1),
(2) Date: Oct. 29, 2020

(87) PCT Pub. No.: WO2019/211208
PCT Pub. Date: Nov. 7, 2019

(65) Prior Publication Data
US 2021/0228373 A1    Jul. 29, 2021

(30) Foreign Application Priority Data

May 1, 2018   (DE) ...................... 10 2018 206 693.0
Jan. 30, 2019  (DE) ...................... 10 2019 201 211.6

(51) Int. Cl.
*A61F 2/44* (2006.01)
*A61F 2/30* (2006.01)

(52) U.S. Cl.
CPC .... *A61F 2/442* (2013.01); *A61F 2002/30133* (2013.01)

(58) Field of Classification Search
None
See application file for complete search history.

(56) References Cited

U.S. PATENT DOCUMENTS 5,554,191 A      9/1996  Lahille et al.
9,883,953 B1 *   2/2018  To ........................... A61F 2/442
(Continued)

FOREIGN PATENT DOCUMENTS

DE           44 16 605 C1    6/1995
DE    10 2017 211 185 A1     1/2018
(Continued)

OTHER PUBLICATIONS

PCT International Search Report for PCT/EP2019/060834 dated Aug. 2, 2019, 4 pages.
(Continued)

*Primary Examiner* — Tessa M Matthews
(74) *Attorney, Agent, or Firm* — DeWitt LLP

(57) ABSTRACT

A place holder for spinal surgery including an upper and lower support having an upper and lower support face which each have a first and a second partial area contacting one another at an edge in a closed state, and an expansion device, by which the lateral extent of the support faces and their vertical distance from one another are variable and the place holder is adjustable between a closed state and an expanded state. A first and the second partial area of the upper and lower support face have mutually engaging structures at the edge where they contact one another in the closed state. The expansion device is designed such that the modification to the lateral extent and to the vertical distance is implemented by operation of a single drive in two mutually independent and freely definable movement profiles coded in the place holder.

26 Claims, 16 Drawing Sheets

(56) References Cited

U.S. PATENT DOCUMENTS

| | | | |
|---|---|---|---|
| 9,913,727 B2* | 3/2018 | Thommen | A61F 2/4425 |
| 2005/0124989 A1 | 6/2005 | Suddaby | |
| 2007/0198089 A1 | 8/2007 | Moskowitz et al. | |
| 2014/0039622 A1 | 2/2014 | Chad et al. | |
| 2015/0148908 A1 | 5/2015 | Marino et al. | |
| 2017/0209282 A1* | 7/2017 | Aghayev | A61F 2/4455 |
| 2019/0117409 A1* | 4/2019 | Shoshtaev | A61F 2/447 |

FOREIGN PATENT DOCUMENTS

| | | |
|---|---|---|
| EP | 2 777 63 0 A1 | 9/2014 |
| FR | 2 719 763 A1 | 11/1995 |

OTHER PUBLICATIONS

English translation of PCT International Search Report for PCTZEP2019/060834 dated Aug. 2, 2019, 2 pages.

* cited by examiner

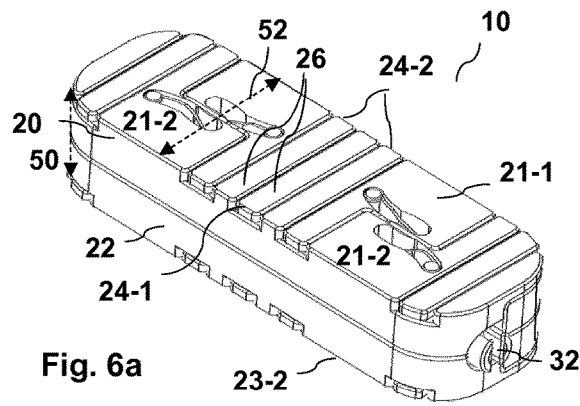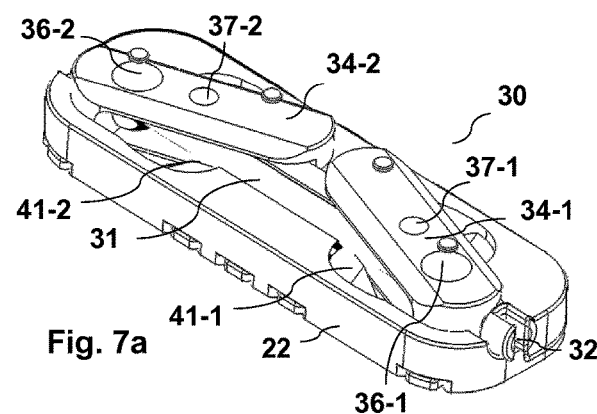
Fig. 6a   Fig. 7a
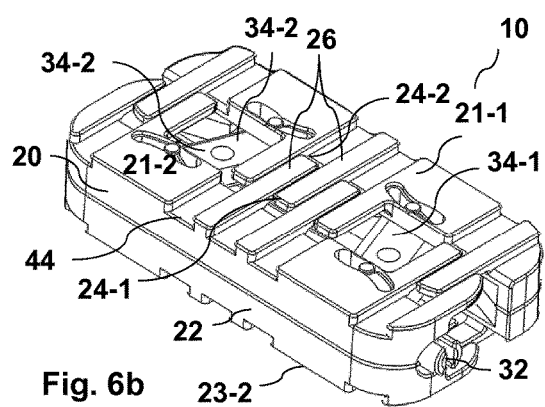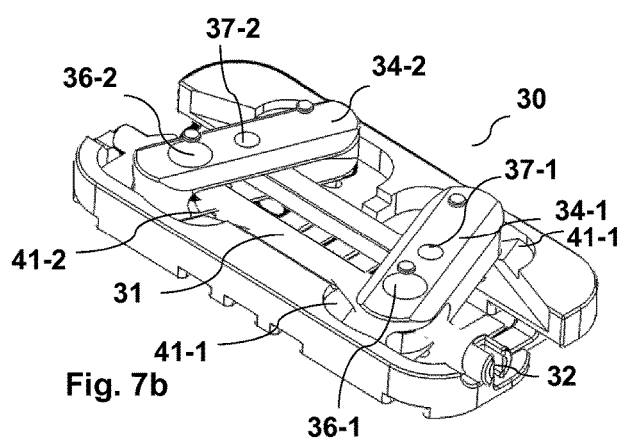
Fig. 6b   Fig. 7b
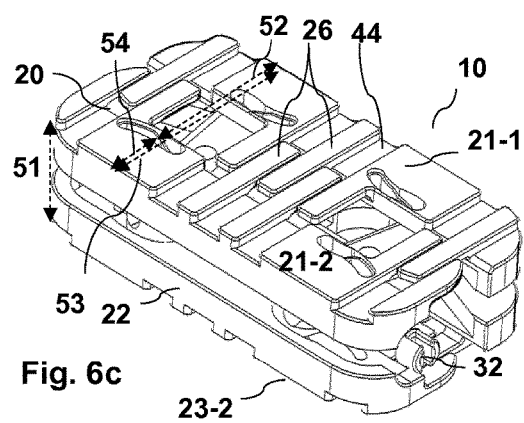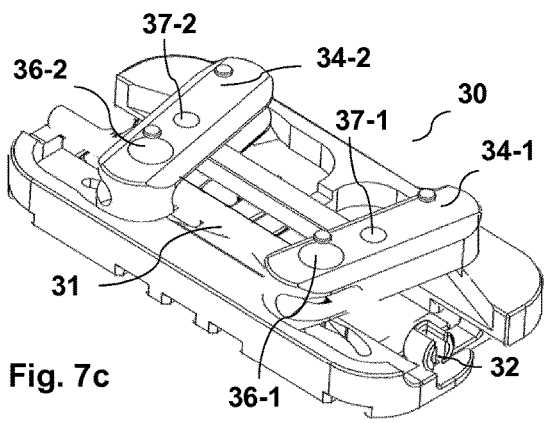
Fig. 6c   Fig. 7c

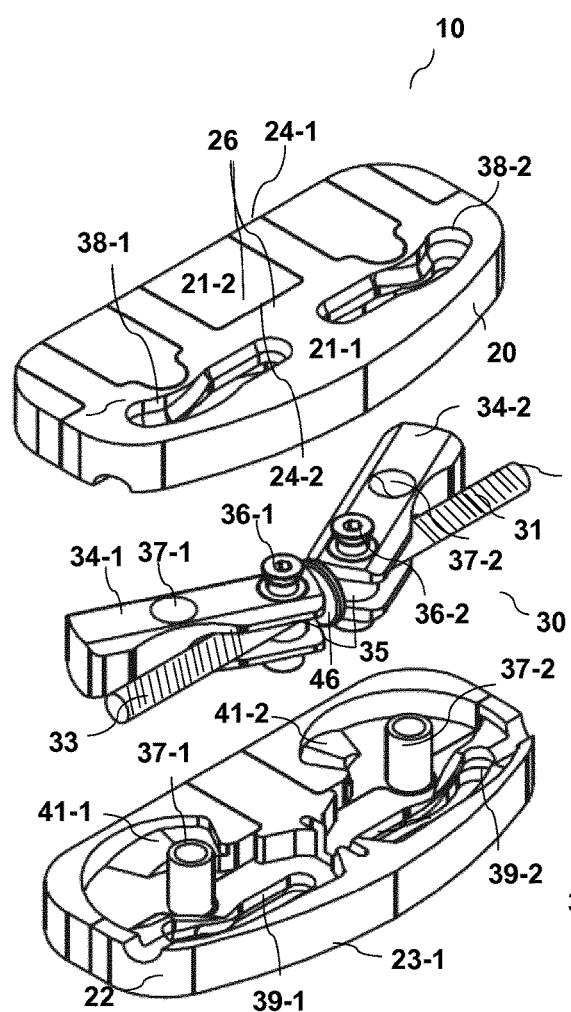
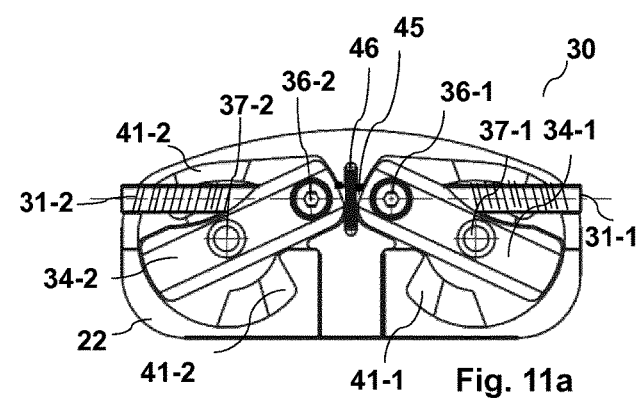
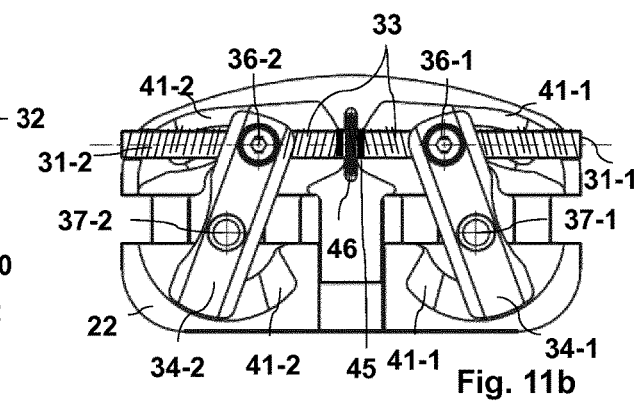
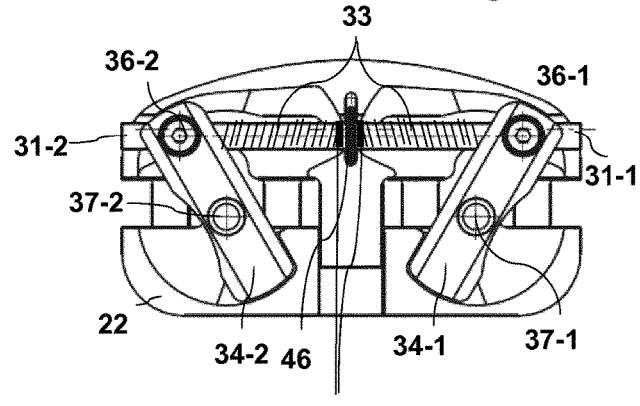
Fig. 10
Fig. 11a
Fig. 11b
Fig. 11c

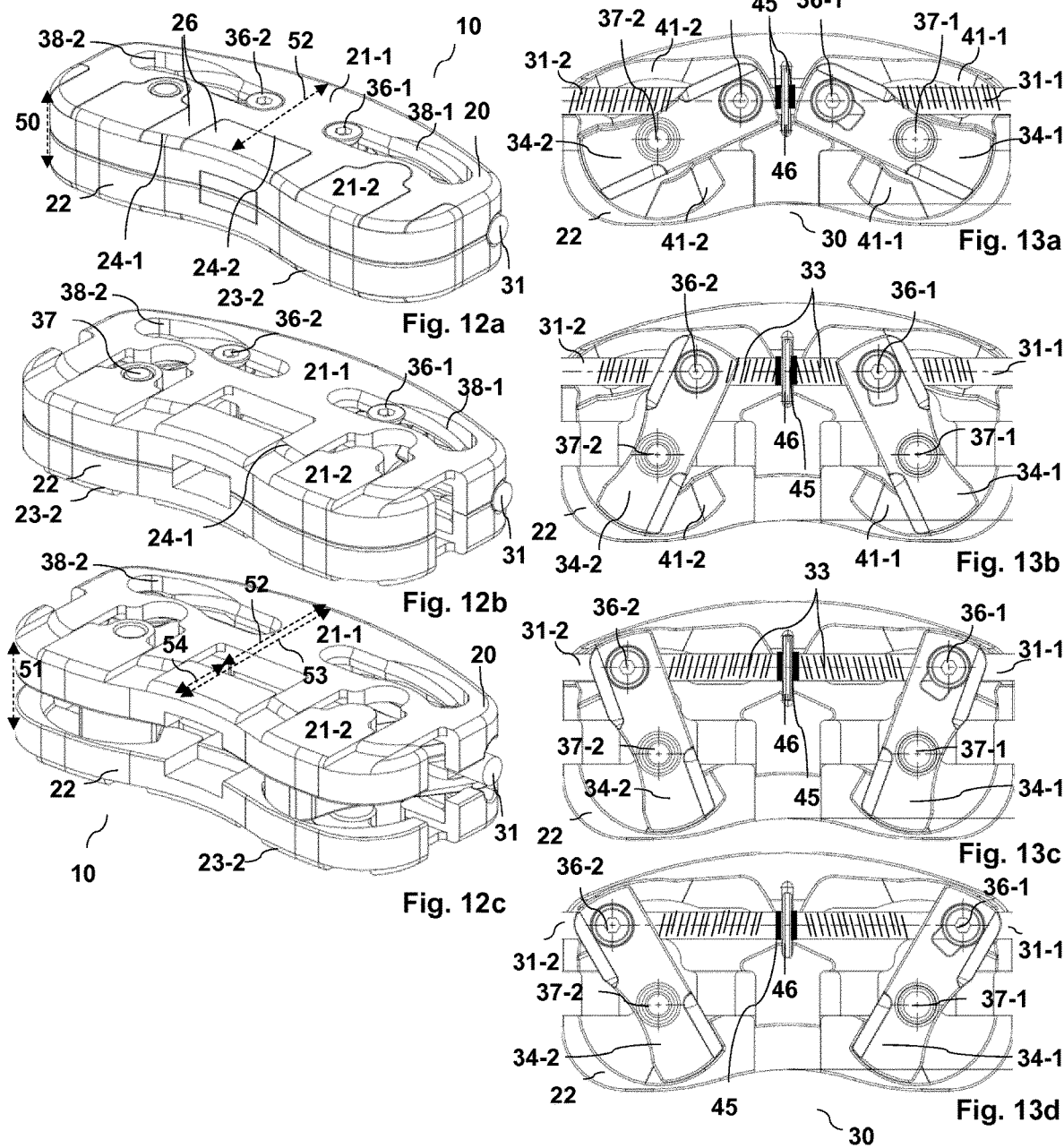

PLACEHOLDER FOR SPINAL SURGERY

RELATED APPLICATIONS

The present application is a National Phase entry of PCT Application No. PCT/EP2019/060834, filed Apr. 27, 2019, which claims priority from German Application No. 10 2018 206 693.0 filed May 1, 2018 and German Application No. 10 2019 201 211.6 filed Jan. 30, 2019, all of these disclosures being hereby incorporated by reference in their entirety.

BACKGROUND

The invention relates to a placeholder for spinal surgery, which comprises an upper support with an upper support surface and a lower support with a lower support surface, the relative position of which can be changed with respect to one another, wherein the upper as well as the lower support surface each have a first and a second sub-surface respectively, which in a closed state of the placeholder touch an edge, and an expansion device, by means of which the support surfaces in their lateral extension can be changed with respect to one another by the first and second sub-surfaces laterally drifting apart between a minimum lateral extension and a maximum lateral extension as well as in their vertical distance between a minimum height and a maximum height of the placeholder, so that the placeholder can be adjusted between a closed and an expanded state.

The degeneration of spinal column segments of the human spinal column is the cause of complaints of the spinal column, which are frequently accompanied by great pain. It is a very typical clinical picture which relates to a large number of patients, frequently in advanced age, and leads to permanent impairments of the patients. In this case, it exhibits a wide variety of manifestations. The most common forms include, on the one hand, the degeneration of the intervertebral disc, that is to say the "wear" of the cartilage-like tissue of the intervertebral disc, as a result of which incorrect positionings occur. On the other hand, this includes osteoporosis, e.g., the decomposition of the interior structure (spongiosa) of the bone, in particular of the vertebra, as a result of which the latter becomes brittle and, as a result, endplate impression fractures and the sintering-in of the vertebral bodies occur.

The treatment is carried out, inter alia, surgically by removing at least part of a degenerated spinal column segment and/or implanting space-holding implants in place of a removed intervertebral disc or a removed intervertebral disc segment or for internal support by implantation into the vertebral body or instead of a vertebral body.

In order to avoid large wounds and thus greater pain and high blood loss, in the surgery, such as spinal surgery, wherever possible microscopic or endoscopic methods are used in order to arrive at the site of occurrence via a small incision. The direct minimally invasive surgical access to the human spinal column dorsally (e.g., from the back of the patient) is simple, quick and safe. In order to damage the innervation of the autochthonic back muscles by the surgical access path as little as possible, the one-sided access path is preferred.

Implants should be compact and adapted to the access path during their introduction to their site of action in the spinal column of a patient, but should be "unfolded" or expanded at the site of action itself to the size required there.

Such space-holding implants—or placeholders—for spinal surgery can replace an intervertebral disc or an intervertebral disc segment. If the placeholder is used as a replacement for the intervertebral disc, it serves as an intervertebral implant for the interbody fusion of vertebrae. This intervertebral implant, which represents the most common application form of the placeholder described here and is also called "cage", must act as a spacer at its site of action and at the same time exert a supporting action—in this case between two adjacent vertebral bodies.

In principle, the use of placeholders described here is also possible for the complete or partial replacement of a vertebral body, wherein the placeholder, when the vertebral body is completely replaced, is used in the sense of a spacer or in the case of partial replacement in the sense of augmentation (e.g., a realignment), a support or a stabilisation of a vertebral body in the vertebral body itself (spondyloplasty). A placeholder, which is used as a complete or partial replacement of a vertebral body, also has to act as a spacer at its site of action and at the same time exert a supporting action—in this case instead of the vertebral body or in the vertebral body itself.

Intervertebral implants exist, e.g., placeholders for spinal surgery, which are used as intervertebral disc replacements, which can be changed in their height: Such intervertebral implants are known, for example, from DE 44 16 605 C1, U.S. Pat. No. 5,554,191 A or FR 2 719 763 A1. These intervertebral implants have in common that two arms of the intervertebral implant are spread apart after their implantation by spacer elements, which are inserted between the arms in the longitudinal direction of said arms and thereby slide along sliding surfaces, which are designed as inclined planes in the form of planar surfaces, so that a different spreading apart of the arms takes place as a function of the depth of the insertion of the spacer element. This results, on the one hand, in a changed angle of the supporting surfaces of the two arms for the adjacent vertebral bodies, which formerly extended parallel to one another (i.e. in the closed state), and at the same time leads to a height of the intervertebral implant, which is changed in asymmetrical form. In the known intervertebral implants of this type, as a rule, centrally mounted screw spindles are used for the displacement of the spacer elements in relation to the symmetry of the intervertebral implant.

In contrast, the documents US 2014/0039622 A1 and EP 2 777 630 A1 describe placeholders for spinal surgery, which can be expanded laterally and vertically in a simultaneous movement. This simultaneous expansion in both the lateral and vertical direction is achieved by spreading upper and lower supports by means of two opposing, preferably pyramidal wedges, which run on a centrally mounted screw spindle. The document US 2005/0124989 A1 also describes an expandable placeholder, which can be expanded laterally and vertically absolutely simultaneously.

Space holders used today for spinal surgery can thus be expanded either laterally or vertically (i.e., only in one direction). Other placeholders used today with a single drive can be expanded laterally and vertically, but only simultaneously and proportionally to one another. A third group of placeholders described so far can be expanded one after the other by means of separate expansion mechanisms, thus with the aid of two drives or with two strictly successive expansion movements, in which the completion of the first movement is the prerequisite for the beginning of the second movement. However, these can only be produced in a very complex manner or are designed in such a way that they do not offer a support surface.

Placeholders, which are expandable only in one direction, for example, only vertically expandable, are either too large for a really minimally invasive operation, if they—used as an intervertebral implant—have the lateral extension from the outset, which are necessary for supporting the vertebral body base plate of the upper vertebral body and the vertebral body endplate of the lower vertebral body, in order to avoid an intrusion into the same. If, on the other hand, space holders, which can be expanded only in one direction, for example, only are vertically expandable, are as compact as necessary for their introduction at their site of action by means of minimally invasive surgery, then they only support sub-surfaces of the vertebral body base plate and of the vertebral body endplate during their vertical expansion and can thus easily break into the latter. When used as a complete or partial vertebral body replacement, there is, in principle, also a risk—from the other side of the vertebral body base plate or the vertebral body endplate—even if minimal.

Placeholders which are also used as an intervertebral implant according to the prior art, which can be expanded simultaneously in both directions, do not banish this risk, since they also already have to expand vertically from the beginning during their lateral expansion and thus already have to exert a large supporting action, even while they have not yet reached their complete laterally necessary extension to do this even without the risk of an intrusion into the vertebral body base plate and/or the vertebral body endplate. In addition, the upper and lower supports are spread into two sections in the case of current conventional placeholders, which can be expanded laterally and vertically at the same time, in such a way that a non-supported surface is in turn produced in the central region, and the respective spread-open sub-sections break into the edge regions of the vertebral body base plate or the vertebral body endplate, since they now only exercise a very local support function.

A placeholder as described in document DE 10 201 7 211 185 A1, which can indeed be expanded laterally and vertically one after the other via a screw spindle but by means of separate expansion mechanisms, can be used as a partial or complete vertebral body replacement as described in the document, but does not offer the necessary support as an intervertebral implant versus the intervertebral disc or the intervertebral disc segment.

All the placeholders described in the prior art are aligned with respect to their shape to a straight implantation or access path and are "unwieldy" for non-straight implantation or access paths. However, if the placeholder is used as an intervertebral implant, it should ideally be able to be introduced from dorsal median or paramedian and come to lie symmetrically neutral to the dural tube (from approximately the second lumbar vertebra to distal) or the spinal cord (up to approximately the second lumbar vertebra), e.g., ventral to the vertebral canal, without passing through the vertebral canal in order not to damage the neurological structures contained therein.

SUMMARY

The object of the invention is therefore to provide and further develop a placeholder for spinal surgery of the type described herein, by means of which the aforementioned problems are overcome. In particular, the disclosure describes a placeholder for spinal surgery, which is used compactly and minimally invasively in corresponding stabilisation processes, such as, for example, in minimally invasive vector lumbar interbody fusion (MIS-VLIF), and can thereby preferably also be implanted in a simple manner via a non-straight implantation path, which can develop the necessary lateral support surface at the site of action, in order to fulfil the support function thereof, and by means of which a desired vertical distance, such as the vertical distance between two vertebral bodies, can be set safely and without risk of intrusion. In addition, the placeholder is intended to take into account the biokinemetric requirements of its use, and to support a natural function of the spinal column in the best possible manner by taking into account the functional anatomy of the movement section to be stabilised.

In addition, corresponding methods for implanting the placeholder in the spinal column of a patient are to be indicated.

The object is achieved according to the invention by the teachings of claims 1 and 4. Further advantageous embodiments and further developments of the invention emerge from the dependent claims.

BRIEF DESCRIPTION OF THE DRAWINGS

FIGS. 6a-6c depict a fifth embodiment of a placeholder according to the invention for spinal surgery in the closed state, in the open state and in the expanded, e.g., open and raised state;

FIGS. 7a-7c depict an interior view of the fifth embodiment of a placeholder according to the invention in the closed state, in the open state and in the expanded, e.g., open and raised state;

FIG. 10 depicts an exploded view of the sixth embodiment of a placeholder according to the invention;

FIGS. 11a-11c depict an interior view of the sixth embodiment of a placeholder according to the invention in the closed state, in the open state and in the expanded, e.g., open and raised state;

FIGS. 12a-12c depict a seventh embodiment of a placeholder according to the invention for spinal surgery in the closed state, in the open state and in the expanded, e.g., open and raised state;

FIGS. 13a-13d depict an interior view of the seventh embodiment of a placeholder according to the invention in the closed state, in the open state, in the opened and partially raised state, and in the expanded, e.g., completely open and raised state;

DETAILED DESCRIPTION

Figure 1A:
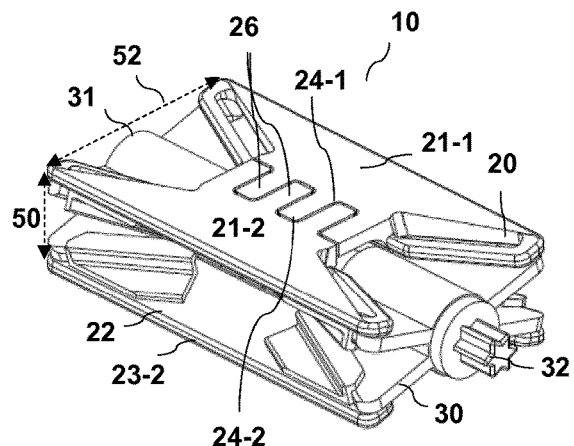
FIGS. 1a-1d depict a first embodiment of a placeholder according to the invention for spinal surgery in the closed state and in the expanded, e.g., open and raised state.
Figure 1B:
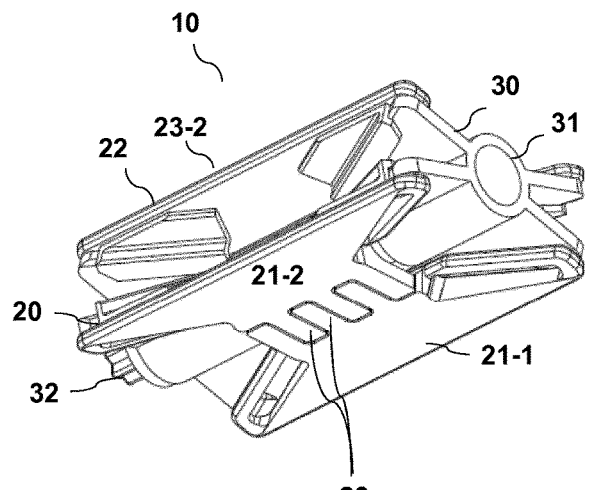
Figure 1C:
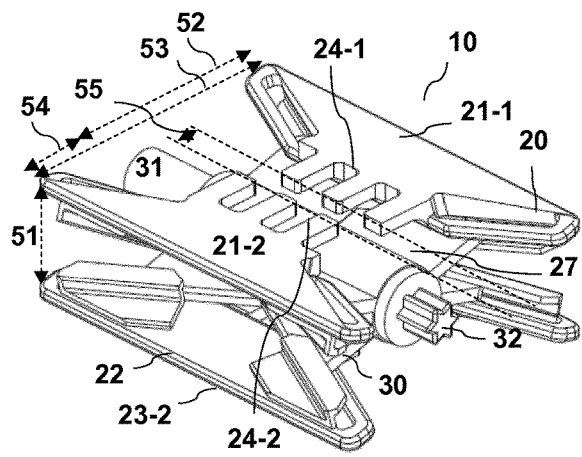
Figure 1D:
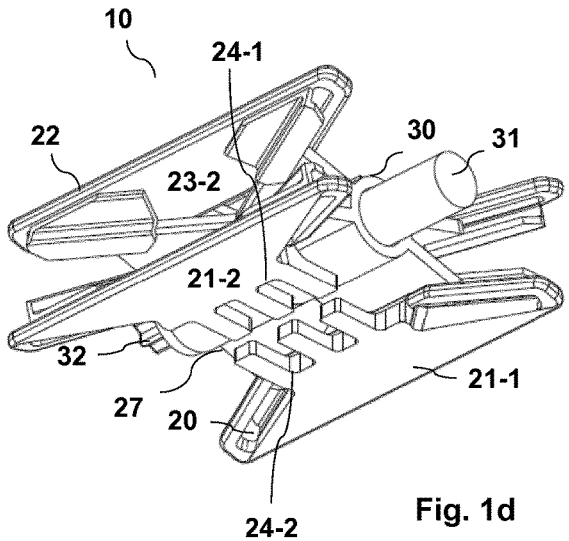

The disclosure describes a placeholder for spinal surgery that comprises an upper support with an upper support surface and a lower support with a lower support surface, the relative position of which can be changed with respect to one another. Both the upper and the lower support surface each have a first and a second sub-surface respectively, which touch an edge in a closed state of the placeholder.

"In each case a first and a second sub-surface" can be read as "in each case at least one first and one second sub-surface". In principle, a further division of the support surfaces is also possible: The first and the second sub-surface would, for example, be able to be subdivided again in a special embodiment into in each case two further-sub surfaces, which then leads to four sub-surfaces of the upper support surface or the lower support surface. However, a division of the upper or lower support surface into in each case more than two sub-surfaces leads as the case may be to a more complicated inner construction of the placeholder.

The closed state of the placeholder is that, in which its lateral and also its vertical extension has a minimum value. In this state—e.g., configured as small or compact as possible—which is the insertion state of the placeholder, the placeholder is introduced into its position in the spinal region through a minimum opening in the back region of the patient.

In this closed state, the upper and lower supports are located at a minimum distance from one another. The same applies to the first and second sub-surfaces of the upper or lower support surface, which, in the closed state, as a rule touch along an edge, since this supports a smallest possible lateral extension of the placeholder. In this case, however, it is not required that there is actually a physical touching of the two edges. As a result, the term "touch" is also intended to encompass a lying side by side of the two edges at a very small distance, typically of less than 1 mm, at most of less than 2 mm. The edge, at which the two sub-surfaces touch (or along which they lie side by side at a very small distance), does not have to be straight, but can assume any form.

The placeholder for spinal surgery further comprises an expansion device, with which the support surfaces in their lateral extension can be changed with respect to one another by a lateral drifting apart of the first and second sub-surfaces of the upper and the lower support surface up to a maximum drift amount between a minimum lateral extension and a maximum lateral extension, as well as in the vertical distance of the upper and the lower support surface between a minimum height and a maximum height of the placeholder (since the upper and lower support surfaces simultaneously represent the upper and the lower limitation of the placeholder) such that the placeholder can be adjusted between a closed and an expanded state. After implantation into the spinal column of the patient, the vertical direction thereby runs approximately parallel to the spinal column or parallel to a direction extending from caudal to cranial. The lateral movement of the sub-surfaces, on the other hand, occurs perpendicular thereto, e.g., in the horizontal.

In order to realise an expansion in the simplest manner after the placement of the placeholder at its site of action in the spinal column of the patient, the expansion device preferably contains a drive, that is, the performance of the expansion, and thus both the change in the lateral extension of the support surfaces and the change in the vertical distance are ideally realised via one and the same drive. The surgeon always uses the same adjusting element. Substantially more complicated in construction, but nevertheless conceivable, is an expansion device with drives which are separate from one another for the change of the lateral extension and the change in the vertical di stance.

The expansion device thus changes both the relative position of the upper support surface to the lower support surface and also the lateral extension of the upper and lower support surface. The term "expanded state" without any addition thereby characterises the maximally expanded state. It may be quite desirable or advantageous to set a partially expanded state. For example, if, after implantation of the placeholder, the latter should not initially have the full vertical distance and/or the support surface should not have the full lateral extension, a partially expanded state can be set in a special embodiment. In turn, each of these partially expanded states can advantageously be fixed, if desired, however a "sliding back" or "refolding" is achieved even by a high self-locking of the expansion device, such as by using, e.g. a thread.

An adjustability of the state between a closed state and an expanded state takes place as a rule continuously, in particular, if no partially expanded states are to be maintained for a longer period of time. Such a continuous adjustability or continuous change in the lateral extension and the vertical distance is advantageous, but not required.

Furthermore, the placeholder according to the invention may also be reset from an expanded state into a closed state—also referred to as an insertion state—and thus permits a simple exchange in the event that the surgeon or the patient is dissatisfied with the result.

In some embodiments of the placeholder, the first as well as the second sub-surface of the upper and the lower support surface at the edge, at which they touch in the closed state, comprises an interengaging structure, which is designed in such a way that it enables lateral drifting apart of the first and second sub-surfaces during an expansion, and, in the expanded state, a lateral gap running perpendicular to the direction of the lateral drifting apart through the upper and also the lower support surface has a gap width, which is smaller than the maximum drift amount.

The interengaging structure of the first sub-surface of the upper support surface is thereby matched to the interengaging structure of the second sub-surface of the upper support surface. The interengaging structure of the first and the second sub-surfaces should therefore be engaged in the closed state.

Preferably, the first and second sub-surface engage with one another as accurately as possible—according to a key-lock principle. The same applies to the interengaging structure of the first sub-surface of the lower support surface and the interengaging structure of the second sub-surface of the lower supporting surface. However, the corresponding structures of the sub-surfaces of the upper support surface and the lower support surface need not be identical or similar. However, identical or similar structures are advantageous, since the expansion behaviour of the upper support surface on the vertebral body base plate of the upper vertebral body and the lower support surface on the vertebral body endplate of the lower vertebral body is identical or similar when the placeholder is used as an intervertebral implant.

In order to allow lateral drifting apart—e.g., a lateral sliding in the opposite direction, the interengaging structures of the first and second sub-surfaces must be designed in such a way that they cannot hook into one another during lateral drifting apart. Ideal structural shapes of such interengaging structures are, for example, a tooth structure, a zig-zag structure or a wavy structure, wherein none of these structures has to be regularly shaped. Finally, the formation of an "ideal" interengaging structure depends on which mapping rule the lateral drifting apart obeys.

The lateral drifting apart thereby occurs preferably by a sliding apart from one another: In the case of a tooth structure, for example, this means that the regions of the interengaging structure of the edges of the first and second sub-surfaces slide apart from one another in the regions of the edges which are aligned parallel to the lateral drift direction, which additionally reinforces the hold, which the support surface continues to offer even during the drifting apart.

The gap width of a lateral gap, which is produced when drifting apart, is thereby smaller or ideally substantially smaller than the maximum drift amount. The lateral gap is thereby the "imaginary" gap which would arise between the first sub-surface and the second sub-surface of the upper support surface or the lower support surface along the entire length of the support surface perpendicular to the lateral drift direction, when straight edges would have been placed inside, which run along the furthest "projecting" regions of the interengaging structure.

If the placeholder is used as an intervertebral body implant, it exerts pressure or supports the vertebral body located above and below, instead of the intervertebral disc. While with straight edges of the first and second sub-surfaces, when drifting apart from the beginning such a lateral gap arises, the gap width of which rapidly assumes a value, in which a support of the vertebral body base plate of the upper vertebral body and of the vertebral body endplate of the lower vertebral body in the central region can no longer be ensured, the interengaging structures according to the invention offer a sufficient support function even in the case of their maximum lateral extension. The interengaging structures of such placeholders according to the invention thus significantly increase the effective impact of the support surfaces in the expanded state with respect to placeholders according to the prior art.

The smaller openings, which are formed instead of a continuous lateral gap, allow a bone consolidation and support the latter by enlarging the surface on which such a consolidation can take place. As a result, the interface between the bone and the implant is improved, which assists the healing of the implant or the integration of such a placeholder into the spinal column.

The main use of the placeholder described here relates to its use as an intervertebral body implant, also called cage or interbody spacer, in order to be implanted instead of the intervertebral disc or instead of sub-regions of the intervertebral disc. For this purpose, the properties of the support surfaces of this placeholder according to the invention are most important.

Nevertheless, further uses of the placeholder according to the invention are possible as a partial or complete vertebral body replacement or also for reinforcing a vertebral body with a bone filler in the sense of a spondyloplasty. The adjustable placeholder is thereby implanted into the vertebral body after opening the cortical bone structure in order to reinforce the vertebral body in the case of fractures or in the case of osteoporosis and then filled.

In a preferred embodiment of the placeholder, the gap width of the lateral gap is zero even in the expanded state. This can be achieved very easily when using a tooth structure, as can be easily understood in the figures. However, many other structural shapes are conceivable, which result in the gap width of the lateral gap being equal to zero even in the expanded state: A wave form with an amplitude that is greater than half the maximum drift amount also satisfies the condition, for example.

In a particularly preferred embodiment, the upper and the lower support of the placeholder are shaped in such a way that, during the lateral drifting apart, the interengaging structure of the first sub-surface slides mounted on a support structure in the part of the support associated with the second sub-surface and the interengaging structure of the second sub-surface slides on a support structure in the part of the support associated with the first sub-surface. This provides additional stability to the support surfaces of the placeholder during their lateral expansion.

A further placeholder for spinal surgery comprises an upper support with an upper support surface and a lower support with a lower support surface, the relative position of which with respect to each other can be changed. Both the upper and the lower support surface in each case have a first and a second sub-surface, which touch an edge in a closed state of the placeholder.

Said additional placeholder for spinal surgery also comprises an expansion device, which contains a drive, by means of which the support surfaces in their lateral extension can be changed by a lateral drifting apart of the first and second sub-surfaces of the upper and the lower support surface to a maximum drift amount between a minimum lateral extension and a maximum lateral extension, as well as in their vertical distance between a minimum height and a maximum height of the placeholder, such that the placeholder can be adjusted between a closed and an expanded state.

Additionally, or alternatively, the above-described properties of the placeholder according to the invention, this further placeholder is characterised in that the expansion device is configured to carry out the change in the lateral extension and the vertical distance in two movement courses, which are independent of one another and freely definable and coded in the placeholder, by means of a single drive.

In the placeholder according to the invention, therefore, the course of the change in the lateral extension and the course of the change in the vertical distance in the course of its expansion are encoded in a freely definable manner—by one and the same conceptual structure—in one and the same expansion device. This means that, for each lateral extension of the upper and lower support surfaces between the minimum and maximum lateral extension, a desired vertical distance of the upper and lower support surfaces from one another can be adjusted within an amount between a minimum height and a maximum height of the placeholder.

In order to realise an expansion in the simplest manner after the placement of the placeholder at its site of action in the spinal column of the patient, the expansion device contains a single drive, that is, the performance of the expansion, and thus both the change in the lateral extension of the support surfaces and the change in the vertical distance of the support surfaces is realised by means of one and the same drive: The surgeon always uses the same adjusting element for this, for example, in linear form, which in turn uses a mechanism for expansion, which does not have to run linearly or not continuously linearly.

Thus, neither the ratio between the change in the lateral extension and the change in the vertical distance have to be kept constant nor do the movements have to be carried out successively or by separate expansion mechanisms or devices.

The placeholder according to the invention preferably comprises a physical image of a flow chart of the change in the lateral extension relative to the change of the vertical distance in the course of its expansion. This can, for example, find its expression in the form of free-form surfaces in the interior or on the inner sides or edges of the upper and also of the lower support or, for example, on spacer elements used for this purpose, which are used as sliding surfaces, in the (freely determinable) form of elongated holes used as sliding holes, or in rotatable structures with different tooth spacing.

Advantageously, in a placeholder according to the invention, the ratio of the change in the lateral extension to the change in the vertical distance in the course of its expansion is changed several times in sections or else continuously. In this case, the change in the lateral extension and in the vertical distance is preferably at least partially separated temporally from one another in such a way that, after its introduction, for example, into a intervertebral disc space of the spinal column of a patient, in which the intervertebral disc has previously been removed, the placeholder introduced in the closed state first experiences a lateral extension, in order to offer a sufficiently wide support surface for the parallel change then commencing somewhat later in the vertical distance between the two vertebral bodies.

In this case, for example, a lateral expansion in relation to the linear drive can be described as a disproportionate extension and thus as a non-linear enlargement of the effective support surfaces, in which initially large changes in the lateral extension are carried out, while a vertical expansion commencing in between and thus a change in the vertical distance then runs linearly or vice versa.

It is also conceivable, that the lateral expansion and the vertical expansion are realised disproportionately and independently of one another by means of a common linear drive.

The manner of the change of the lateral extension of the support surfaces in order to change their vertical distance can be adapted, if necessary, to the uses, the specific problems of the patient, but also to the wishes of the surgeon in charge. A series of placeholder models can thereby be created, which represent frequently used constellations, all work according to the same principle, but differ, for example, in the formation of the free-form surfaces and/or the formation of the elongated holes used as sliding holes.

The use of free-form surfaces and/or elongated holes used as sliding holes also offers the possibility of fixing or stabilising certain states in a simple manner by the vertical distance being briefly reduced again by means of the formation of the free-form surfaces and/or of the elongated holes used as sliding holes, and thus a metastable state is achieved.

Furthermore, the placeholder according to the invention can preferably also be reset from an expanded state into a closed state—also referred to as an insertion state —, the lateral extension of the upper and lower support surfaces can therefore be set back from a maximum extension to a minimum extension and the vertical distance of the upper and lower contact surfaces can be set back from a maximum height to a minimum height, by the drive of the expansion device being operated in the opposite direction.

With the placeholders according to the invention with a lateral gap running through the upper and also the lower support surface having a gap width, which is (significantly) smaller than the maximum drift amount of the lateral extension of these support surfaces and/or with an expansion device, which is able to carry out the change in the lateral extension and the vertical distance in two independent and freely definable movement courses, a minimally invasive implantable placeholder is described, which can develop the necessary size of the support surface at the site of action, in order to fulfil the support function thereof, and by means of which a desired vertical distance, such as the vertical distance between two vertebral bodies, can be set safely and without risk of intrusion. It thereby takes into account the biokinemetric requirements of its use and supports a natural function of the spinal column in the best possible way, by improving the sagittal balance.

It offers a significantly larger effective support than placeholders according to the prior art, which are introduced dorsally, in particular, a significantly more functionally distributed support surface with improved footprint and optimal press fit (e.g., better "anchorage" in the spinal column due to its shape and the pressure exerted and its distribution). The placeholder according to the invention thereby takes into account the biologically derivable optimal expansion behaviour by means of a freely definable expansion course of the change in the lateral extension, e.g., its expansion into the width, which, after the placeholder has been brought into place, is preferably started first at its site of action, and the change in the vertical distance, e.g., its expansion, into the height, which is preferably somewhat delayed or subsequently introduced, although this is carried out with the same drive. The placeholder according to the invention thereby combines a plurality of properties, which are in principle required by a placeholder for implantation in the spinal column.

The essence of the invention is therefore also an expansion mechanism, which makes the lateral and vertical expansion designable independent of one another, but nevertheless has only one drive for realising the expansion. The expansion mechanism of the placeholder allows the two expansion qualities to be set out or coded in their sequence and in any proportionality with respect to one another technically in the placeholder.

In a preferred embodiment of the placeholder or the placeholder described above, the expansion device for setting the placeholder between the closed and the expanded state contains a screw spindle with a screw head, by means of which the change in the lateral extension and also of the vertical distance can be controlled.

In this embodiment, the screw spindle is therefore the essential element of the drive of the expansion device. Access can be gained via the screw head to the screw spindle by means of a tool which supports the minimally invasive surgery. For this purpose, the screw head can have any shape and design, which makes it possible to engage with the tool introduced from the outside, in order to achieve a rotational movement of the screw spindle and also to be able to control it correspondingly, in order to thus in turn control the change in the lateral extension and also of the vertical distance.

The axis of the screw spindle thereby does not have to run centrally or in the middle in the placeholder. Rather, it can assume any desired position, preferably perpendicular to the direction of the lateral extension. It can thereby be placed in such a way that the screw head of the screw spindle can be reached more easily after the insertion of the placeholder at its site of action than for placeholders according to the prior art, which require a central position of such a drive element. In this embodiment, the screw spindle of the drive moves in the sense of an axis of rotation which is changed in its position, therefore as a technically realised centrode or polhode.

By means of the screw spindle, the expansion of the placeholder can be carried out in the simplest manner, if it is in turn part of a wedge mechanism or is a mechanism based on the principle of wedge and counter-wedge, with which the change in the lateral extension and also of the vertical distance of the contact surfaces is carried out simultaneously.

In significantly more advantageous embodiments, however, the rotation of the screw spindle allows an expansion of the placeholder in such a way that the change in the lateral extension and the vertical distance takes place in two movement courses, which are independent of one another and freely definable. In particular, it enables the at least partial or complete separation of the change in the lateral extension and the vertical distance from one another with regard to their sequence in relation to each other.

In a special embodiment of the placeholder, the latter has no symmetries along an axis which runs parallel to the axis of the screw spindle, in any lateral cutting plane. A parallel course thereby also includes a position on the axis of the screw spindle.

In a particularly preferred embodiment of the placeholder according to the invention, its expansion device further comprises a movable spacer element. Such a spacer element spaces two movable parts apart, in such a way that a relative movement of the two parts relative to one another can take place only along predetermined paths or only in predetermined regions. Such a spacer element can be a cam or have a cam-like shape, but can also assume other, more specific geometric shapes. However, the movable mounting of the spacer element in each of the two movable parts is important.

In this case, this spacer element is now mounted at a position on the spacer element, preferably at a first end, in a laterally rotatable manner about a movable axis which can be displaced along the screw spindle by means of a threaded nut, which is integrated into the movable axis and runs on a thread of the screw spindle (which is accordingly an external thread), wherein the movable axis is arranged running directly or indirectly in an upper elongated hole in the first sub-surface of the upper support and in a lower elongated hole in the first sub-surface of the lower support.

"Arranged directly in an elongated hole" means thereby that the axis runs directly in the elongated hole, "arranged indirectly in an elongated hole" means that an element connected to the axis runs in the elongated hole.

The spacer element is furthermore mounted so as to be laterally rotatable about a fixed axis, which is mounted in the second sub-surface of the upper support and in the second sub-surface of the lower support in a laterally positionally invariable manner. This fixed axis is preferably located in its central region. However, an arrangement of the fixed axis at a second end of the spacer element is also possible. There is also the possibility of realisation with a non-fixed axis.

And finally, the spacer element is mounted on a first and/or a second end in a freely sliding manner on an upper three-dimensional sliding surface below the first and/or the second sub-surface of the upper support and on a lower three-dimensional sliding surface above the first and/or second sub-surface of the lower support, wherein the upper three-dimensional sliding surface and the lower three-dimensional sliding surface are shaped relative to one another in such a way, that, for each angle of rotation of the spacer element about the fixed axis, the first and/or second end of the spacer element assumes a defined position on the upper and also on the lower three-dimensional sliding surface, the absolute position of which and the corresponding position of the movable axis in the correspondingly shaped elongated holes determines the lateral extension of the placeholder and the distance of which between the upper and the lower three-dimensional sliding surfaces relative to one another in the closed state determines the height of the placeholder.

A three-dimensional sliding surface is a surface which is formed in the three-dimensional space, which—as already explained above—is shaped in a preferred embodiment in such a way that it forms the lateral and vertical movement course in combination with a further three-dimensional sliding surface and/or the shape of the elongated hole used as a sliding hole.

In a further particularly preferred embodiment of the placeholder according to the invention, its expansion device comprises a movable spacer element, which can be moved along the screw spindle and has four guide elements, which in each case are displaceable in a first upper elongated hole and/or below a first upper guide sliding surface in the first sub-surface and in a second upper elongated hole and/or below a second upper guide sliding surface of the second sub-surface of the upper support and in a first lower elongated hole and/or on a first lower guide sliding surface of the first sub-surface and in a second lower elongated hole and/or on a second lower guide sliding surface of the second sub-surface of the lower support. In this embodiment, the spacer element comprises upper and lower three-dimensional sliding surfaces. The upper sliding surface and the lower sliding surface are thereby formed on the spacer element in relation to each other, and the elongated holes and/or guide sliding surfaces are shaped and arranged in each of the sub-surfaces of the upper and lower supports, such that for a defined position, which the spacer element assumes on the screw spindle, the corresponding position of the guide elements in the correspondingly shaped elongated holes and/or guide sliding surfaces determines the lateral extension of the placeholder and the distance of which between the upper and lower sliding surfaces on the spacer element at a touching edge and/or at a position of the upper and lower guide sliding surfaces of the upper and lower supports associated with the position of the spacer element determines the height of the placeholder. Guide sliding surfaces are thereby special sliding surfaces, which are designed in such a way that, in addition to the vertical positioning (and thus the degree of vertical expansion of the placeholder), they also assume the lateral positioning (and thus the degree of lateral expansion of the placeholder).

Preferably, shaped elements on the upper and/or the lower three-dimensional sliding surface and/or the shaping of the elongated hole thereby enable a relative fixing of specific, predetermined positions.

Furthermore, in a variant of this embodiment of the placeholder according to the invention, a combination of the shaping of the sliding surfaces on the spacer element and a shaping on an inner side of the upper and lower support is possible here for the change of the vertical distance.

In a third particularly preferred embodiment of the placeholder according to the invention, its expansion device further comprises a movable double pair of spacer elements, which are mounted in a position on each spacer element of the double pair in a laterally rotatable manner about a movable axis, wherein the movable axes are arranged on a threaded nut, and can be displaced along the screw spindle be operation of the threaded nut running on a thread of the screw spindle. Furthermore, the first spacer element of the double pair is laterally rotatable about a fixed axis, which is mounted in the first sub-surface of the upper support and in the first sub-surface of the lower support in a laterally positionally invariable manner, and the second spacer element of the double pair is laterally rotatable about a fixed axis, which is mounted in the second sub-surface of the upper support and in the second sub-surface of the lower support in a laterally positionally invariable manner.

A pair of spacer elements is thereby therefore a pair of a first spacer element and a second spacer element, wherein the first and second spacer elements in each case comprise an upper spacer element directed towards the upper support and a lower spacer element directed towards the lower support, which move together (e.g., that is, parallel to one another about the same axial positions).

The threaded nut running on the thread of the screw spindle is thereby designed in such a way that the nut comprises sliding surfaces or a double toggle lever structure for the first and second sub-surfaces of the upper support and for the first and second sub-surfaces of the lower support, which are mounted in a freely sliding manner on guide sliding surfaces of the first and second sub-surfaces of the upper support and on guide sliding surfaces of the first and second sub-surfaces of the lower support.

The angular position between the first spacer element and the second spacer element then determines the lateral extension of the placeholder and a distance of the upper and the lower sliding surface relative to one another or a position of the double toggle lever structure at a touching edge (and thus also an opening angle of the toggle lever structure) and/or at a position of the upper and lower guide sliding surfaces of the upper and lower supports associated with the position of the threaded nut determines the height of the placeholder.

Furthermore, it is particularly advantageous, when the placeholder, which contains a screw spindle as an essential element of the drive of the expansion device, is designed in such a way that this screw spindle has on its second half a thread, which is opposite a thread on the first half of the screw spindle, and the expansion device comprises a first spacer element or a first double pair of spacer elements, which uses the first half of the screw spindle, and a second spacer element or a second double pair of spacer elements, which uses the second half of the screw spindle. The respective maneuverability of the thread of the screw spindle depends on how the corresponding spacer element or double pair of spacer elements is mounted relative to the axis of this screw spindle.

First or second upper and lower three-dimensional sliding surfaces and corresponding upper and lower elongated holes and/or guide sliding surfaces are thereby associated with the first or second spacer element or double pair of spacer elements. Optionally, in each case one or two first or one or two second movable axes and one or two first or one or two second fixed axes are also associated with the first or second spacer element or double pair of spacer elements.

A placeholder designed in such a way thus permits a two-sided expansion- and support function, which increases the stability of the placeholder and prevents a "tilting away" of the placeholder. The first half and the second half of the screw spindle and of the elements associated with it do not thereby have to be designed symmetrically with respect to one another.

However, it is particularly advantageous, if, in a placeholder with a first and a second spacer element or double pair of spacer elements, the first and the second spacer element or double pair of spacer elements are designed and arranged mirror-images with respect to one another. The placeholder can then, therefore, have an axis of symmetry, which runs perpendicular to the axis of the screw spindle. Such a mirror-image operation permits a particularly high stability, in particular, when the placeholder is brought as an intervertebral implant centrally into the intervertebral disc space between two vertebral bodies and is expanded there.

Alternatively, however, it is also possible that the first and the second spacer element or double pair of spacer elements are designed and arranged in the same direction with respect to one another in a placeholder with a first and a second spacer element or double pair of spacer elements.

In a placeholder having a first and a second spacer element, a screw spindle used as a drive element can be subjected to tension, in order to guide the spacer elements relative to one another during the expansion. However, it can also be subjected to pressure, in order to guide the spacer elements away from one another during the expansion.

In a particularly preferred embodiment of the placeholder according to the invention, the screw spindle thereof has a guide structure between the first and second half and/or between the first and second spacer element or double pair of spacer elements, which is mounted in a retaining element to be rotatable but not laterally displaceable, wherein the retaining element is mounted movably, in particular vertically movably, but in turn laterally not displaceable in its position in the upper and in the lower support. This serves to centre the expansion device with respect to the supports.

The placeholder according to the invention can be maximally individualised in one embodiment: The shape and position of the three-dimensional sliding surfaces and the shape and position of the elongated hole and/or of the guide sliding surfaces are thereby designed according to an individually required expansion behaviour. Such a placeholder can be produced individually on demand according to the properties required by the patient or the behaviour preferred by the surgeon: For this purpose, first examination data of the patient are recorded, which comprise both geometric data of the problem existing in the patient and data characterising the spinal material, such as, for example, local bone density and brittleness. In addition, the surgeon in charge can store further requirements, which he considers necessary for the best possible surgical intervention and for an optimal function. From these data, an optimal size of the placeholder in the closed state and in the expanded state, optionally an optimal interengaging structure and an optimal course of movement of the change in the lateral extension and the change in the vertical distance of the upper and lower support surfaces are determined in a manner independent of one another, and physical coding of the placeholder, for example, the formation of free-form surfaces as sliding surfaces and the formation of elongated holes as sliding holes, is determined therefrom. This type of individual determination of the optimal placeholder for the patient and/or the surgeon can also be the contents of a planning unit or a corresponding computer program product provided for this purpose.

A placeholder, which is particularly optimised for implantation by means of a minimally invasive operation, has a kidney-shaped (or bean-shaped) form in a top view. Such a placeholder therefore has, laterally at most, a mirror axis/axis of symmetry, which runs parallel to the direction of the lateral extension.

The kidney-shaped or bean-shaped form simplifies the implantation in an arcuate implantation path for a ventrally transversely extending implantation for interbody fusion.

However, such a shape is not necessary for an oblique, but rectilinearly extending implantation in the intervertebral disc space.

In the case of only partial surgical resection of the vertebral joint (facetotomy), an arcuate implantation path with an implantation tunnel of approximately 8 mm height and 13 mm width results. According to biokinemetric analyses, implant heights of between 7 and 14 mm are required in the interbody fusion of the lumbar spine.

In one embodiment, the placeholder according to the invention has a minimum height of greater than or equal to 7 mm in the closed state and a maximum height of less than or equal to 14 mm in the expanded state and a lateral extension, therefore an extension parallel to the direction of the lateral drifting apart, of greater than or equal to 13 mm in the closed state. In addition, it preferably has a lateral extension of less than or equal to 25 mm in the expanded state, but greater lateral extensions in the expanded state are also possible.

A series of placeholders according to the invention is preferably available, which can use different height ranges. Advantageous here is, for example, a small model of the placeholder, which makes possible a minimum height of 7 mm and a maximum height of 11 mm, and a large model of the placeholder, which makes possible a minimum height of 9 mm and a maximum height of 14 mm. Small and large models of the placeholder can then in turn be obtained in kidney-shaped form or in principle be cuboidal in shape. All models can also be obtained in different adjustment stages of the change in the lateral extension and the vertical distance.

In summary, the placeholder according to the invention takes into account the technical requirement, which results from a biokinemetric consideration of the intended surgical fusion of two lumbar vertebral bodies with one another, wherein at the same time the following have been considered:

The possible surgical access path and the resulting space conditions.

The functional anatomy of the movement section to be stabilised.

The possible directions of movement of the implantation process within the surgical access path.

The optimum extent of the implant according to biokinemetric criteria.

The placeholder according to the invention in its various embodiments is preferably made of titanium. Titanium is one of the materials, which are particularly preferred in surgery because of its resistance and good compatibility, and the mechanism of the placeholder described here allows all of its parts to be constructed in titanium. However, a design in ceramic, or a production with polymers of the group of polyether ketones (PEK), such as, for example, polyether ether ketone (PEEK) or in polyether ketone ketone (PEKK), is also possible.

In a method according to the invention, the placeholder, which is used as an intervertebral implant, is introduced minimally invasively after removal of the intervertebral disc (by means of facetotomy between a vertebral body base plate of the upper vertebral body and a vertebral body endplate of the lower vertebral body in place of the intervertebral disc, in such a way that the adjusting element of the expansion device of the placeholder, in a specific embodiment the screw spindle with its screw head, remains reachable with a tool. If the placeholder is in the desired position, the screw spindle is continuously rotated with the tool via the screw head. In this case, the placeholder preferably first expands into the width, in order to provide the vertebral body base plate of the upper vertebral body and the vertebral body endplate of the lower vertebral body with the greatest possible corresponding support, in order to prevent an intrusion or delayed sintering-in. Subsequently,—or firstly, in addition to a continuation of the lateral expansion—the expansion of the placeholder into the height is initiated by continued rotation of the screw spindle. In a preferred embodiment, this vertical expansion can also be continued after the lateral expansion has already been completed, therefore the placeholder has reached its maximum lateral extension—in turn by continued rotation of the screw spindle always in the same direction until the maximum height of the placeholder is reached. In the extreme case, the vertical expansion can also begin only when the lateral expansion is completed. After this, the tool is removed from the wound opening, and the placeholder remains firmly in place (instead of the intervertebral disc) between the vertebral body base plate of the upper vertebral body and the vertebral body endplate of the lower vertebral body, which are now supported at the correct distance from one another by the expanded placeholder.

FIGS. 1a-1d show a first embodiment of a placeholder 10 according to the invention for spinal surgery in two perspective views in each case in the closed state and in the expanded state, e.g., open and raised state, which comprises an upper support 20 with an upper support surface 21 and a lower support 22 with a lower support surface 23, the relative position of which can be varied with respect to one another, wherein the upper 21 and the lower support surface 23 each have a first 21-1, 23-1 and a second sub-surface 21-2, 23-2, which touch an edge 24-1, 24-2, 25-1, 25-1 in a closed state of the placeholder 10. The placeholder also comprises an expansion device 30, with which the support surfaces 21, 23 can be varied relative to one another in their lateral extension by lateral drifting apart of the first 21-1, 23-1 and the second sub-surface 21-2, 23-2 up to a maximum drift amount 54 between a minimum lateral extension 52 and a maximum lateral extension 53 as well as in their vertical distance between a minimum height 50 and a maximum height 51 of the placeholder 10, so that the placeholder 10 can be adjusted between a closed and an expanded state.

In order to realise an expansion in the simplest manner after the placement of the placeholder 10 at its site of action in the spinal column of the patient, the expansion device 30 contains a single drive, that is, the performance of the expansion, and thus both the change in the lateral extension of the support surfaces 21, 23 and the change in the vertical distance are realised via one and the same drive. As an essential element, this drive has a screw spindle 31, by means of which the expansion of the placeholder 10 can be carried out. In this first embodiment of a placeholder 10 according to the invention, the screw spindle 31 is part of a wedge mechanism or more precisely a mechanism which is based on the principle of wedge and counter-wedge, by means of which the change in the lateral extension and also of the vertical distance of the support surfaces 21, 23 is carried out simultaneously and in a manner dependent on one another—in the same ratio to one another.

Two imaginary straight pyramids are opposite one another at a defined distance from the tip to tip in a mirror-imaged manner in such a way that their two heights lie on a common straight line. In each case two mutually opposite, materially formed side edges form the wedges, which change a common counter-wedge ($\nabla$ nabla) in its spatial position when the pyramids approach one another.

The placeholder can, as a spinal implant in the sense of a spacer or intervertebral implant, replace a intervertebral disc or a vertebral body in the sense of an vertebral body replacement, or can also be used in the sense of an augmentation of a vertebral body in the vertebral body itself (spondyloplasty).

The first 21-1, 23-1 and the second sub-surface 21-2, 23-2 of the upper 21 and the lower support surface 23 have an interengaging structure 26 in the form of interengaging teeth on the edge 24-1, 24-2, 25-1, 25-1, at which they touch in the closed state. This structure is thus designed in such a way that it permits a lateral drifting apart of the first 21-1, 23-1 and second sub-surfaces 21-2, 23-2 during expansion and, in the expanded state, a lateral gap 27 running perpendicular to the direction of lateral drifting apart through the upper 21 and the lower support surface 23 has a gap width 55, which is smaller than the maximum drift amount 54.

Figure 2A:
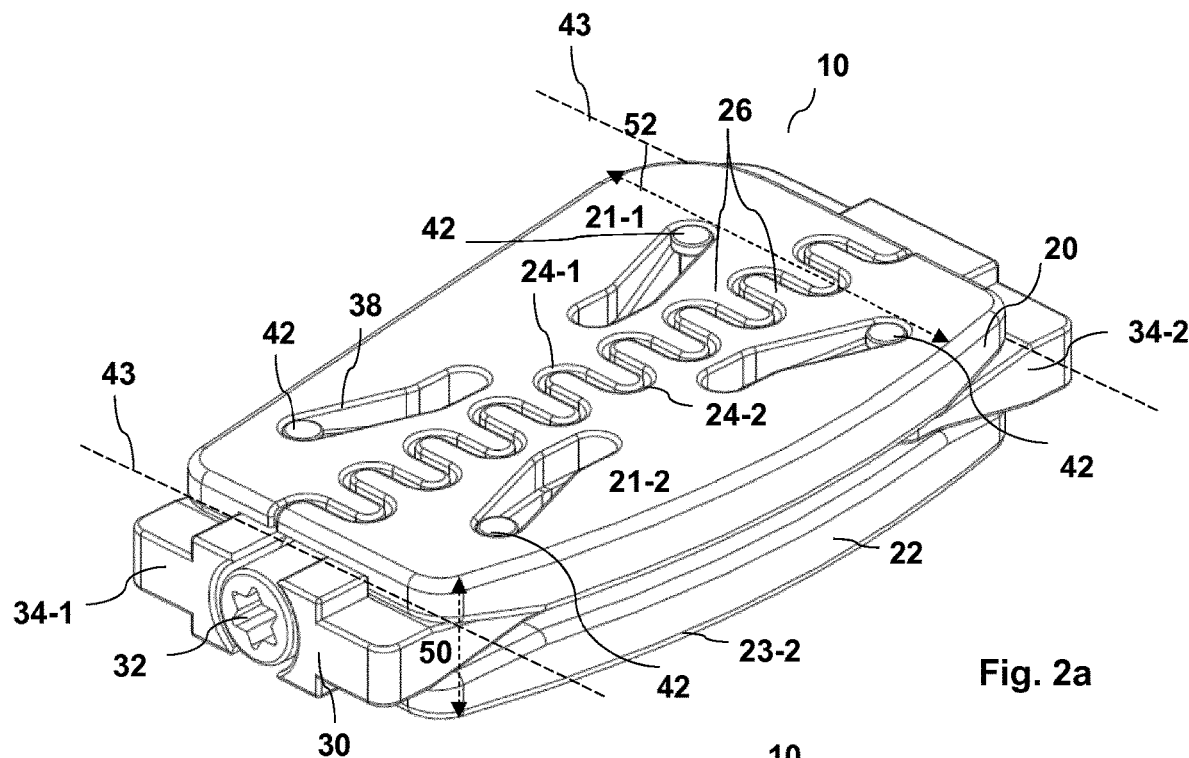
FIGS. 2a and 2b depict a second embodiment of a placeholder according to the invention for spinal surgery in the closed state and in the expanded state.
Figure 2B:
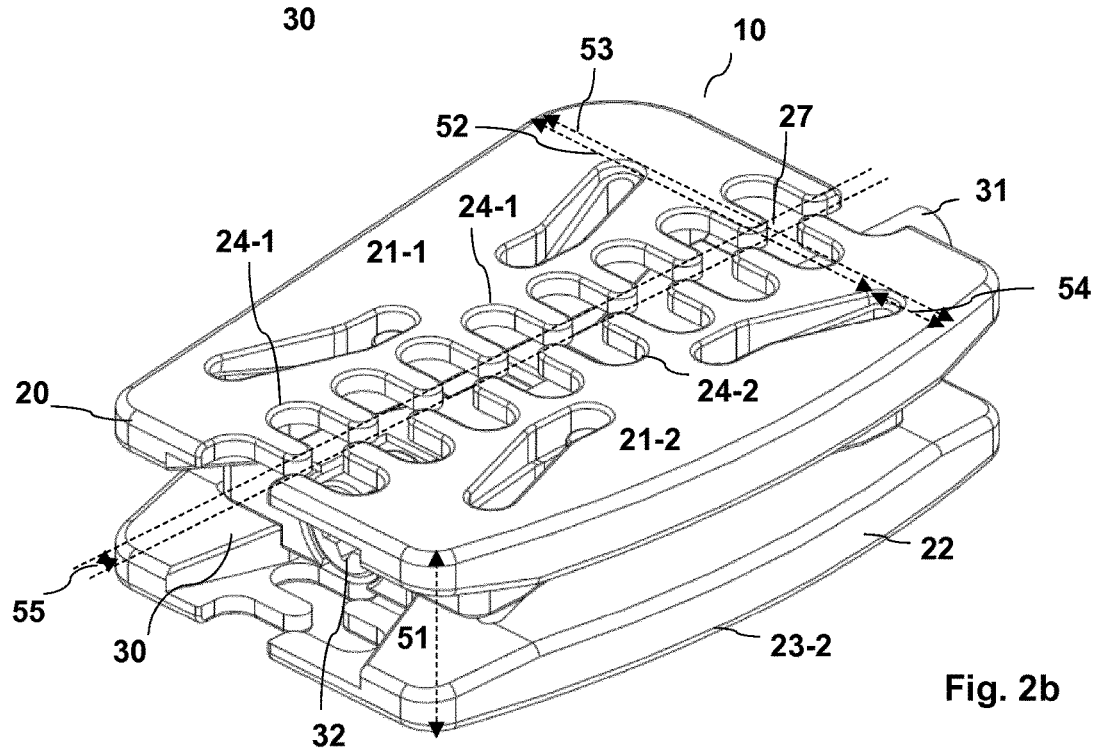

In FIGS. 2a and 2b, a second embodiment of a placeholder 10 according to the invention for spinal surgery is shown in a perspective view in the closed state and in the expanded state. This placeholder 10 in turn comprises an upper support 20 with an upper support surface 21 and a lower support 22 with a lower support surface 23, the relative position of which can be varied with respect to one another, wherein the upper 21 and the lower support surface 23 in each case have a first 21-1, 23-1 and a second sub-surface 21-2, 23-2, which in a closed state of the placeholder 10 touch an edge 24-1, 24-2, 25-1, 25-1. The placeholder also comprises an expansion device 30, with which the support surfaces 21, 23 can be changed in their lateral extension through lateral drifting apart of the first 21-1, 23-1 and the second sub-surface 21-2, 23-2 up to a maximum drift amount 54 between a minimum lateral extension 52 and a maximum lateral extension 53 as well as in their vertical distance between a minimum height 50 and a maximum height 51 of the placeholder 10 relative to one another, so that the placeholder 10 can be adjusted between a closed and an expanded state.

In this second embodiment of the placeholder 10 according to the invention, the first 21-1, 23-1 and the second sub-surface 21-2, 23-2 of the upper 21 and of the lower support surface 23 at the edge 24-1, 24-2, 25-1, 25-1, at which they touch in the closed state, have a wave-shaped interengaging structure 26. This structure is also designed in such a way that, in the event of an expansion, it enables a lateral drifting apart of the first 21-1, 23-1 and second sub-surface 21-2, 23-2, and in the expanded state has a lateral gap 27 running perpendicular to the direction of the lateral drifting apart through the upper 21 and also the lower support surface 23 has a gap width 55, which is substantially smaller than the maximum drift amount 54. In the closed state of the placeholder 10, the interengaging structures of the first and second sub-surface of the upper and also of the lower support surfaces show an interengaging according to the "key-lock principle" over the entire length of the placeholder, so that, in the closed state, the upper and also the lower support surface can be realised as in each case one continuous surface.

The expansion device 30 of this second embodiment of the placeholder 10 according to the invention is now also configured to carry out the change in the lateral extension and the vertical distance in two movement courses which are independent and freely definable, but by means of a single drive. For this purpose, the expansion device of the placeholder 10 comprises a movable spacer element 34, which is movable along the screw spindle 31 by rotation of the screw head 32 and has four guide elements 42 in the form of mushroom head bolts, which in each case are displaceable in a first upper elongated hole 38 in the first sub-surface 21-1 and in a second upper elongated hole 38 of the second sub-surface 21-2 of the upper support 20 and in a first lower elongated hole 39 of the first sub-surface 23-1 and in a second lower elongated hole 39 of the second sub-surface 23-2 of the lower support 22.

The spacer element 34 itself has upper and lower three-dimensional sliding surfaces 40, 41, which are formed on the spacer element 34 with respect to one another, and the elongated holes 38 in each of the sub-surfaces of the upper and lower support are shaped and arranged in such a way, that for each defined position, which the spacer element 34 assumes on the screw spindle 31, the corresponding position of the guide elements 42 in the form of the mushroom head bolt in the correspondingly shaped elongated holes 38, 39 determines the lateral extension of the placeholder 10 and the distance between the upper 40 and the lower three-dimensional sliding surface 41 relative to one another in each case on the spacer element 34 at a touching edge 43 of the upper 20 and of the lower support 22 determines the height of the placeholder 10. Since the inner side of the upper and lower supports 20, 22 also has a shape in this embodiment, the touching edge 43 thereby "migrates" during the expansion of the placeholder.

The expansion device 30 comprises a first spacer element 34-1 that uses the first half of the screw spindle and a second spacer element 34-2 that uses the second half of the screw spindle 31, wherein first or second upper and lower three-dimensional sliding surfaces and corresponding upper 38 and lower elongated holes 39 are associated with the first 34-1 and the second spacer element 34-2.

This second embodiment of the placeholder 10 according to the invention therefore operates specifically with a wedge and counter-wedge principle, however, by a sliding of the supports formed on the inner sides onto the freely formed sliding surfaces of the wedges and the mushroom heads arranged thereon in accordance with the desired vertical movement sequence, which can slide as guide elements 42 in freely formed elongated holes 38, 39 in accordance with the desired lateral movement sequence in the sub-surfaces 21-1, 21-2, 23-1, 23-2 of the upper and lower supports 20, 22, the hitherto fixed ratio of the lateral to vertical expansion is broken by using a wedge and counter-wedge principle, so that the wedges act as corresponding spacer elements 34-1, 34-2.

The sub-surfaces of the supports can run within the nablas and deltas (due to their spatial expansion or shaping) on lanes which reproduce the expansion in width and height. Even if the wedges and the inner sides of the supports have flat sliding surfaces and thus a linear change in the vertical distance is achieved, the flow chart of the lateral extension thereof is set down independently in the configuration of the elongated hole. This can thus take place non-linearly in such a way that firstly a rapid lateral extension is used, while when a certain vertical distance is reached (and—when used as an intervertebral implant—build-up of a certain pressure on the placeholder by the upper and lower vertebral bodies) only a small lateral extension takes place and finally the last region of the change in the vertical distance can take place without any further change in the lateral extension.

Figure 3A:
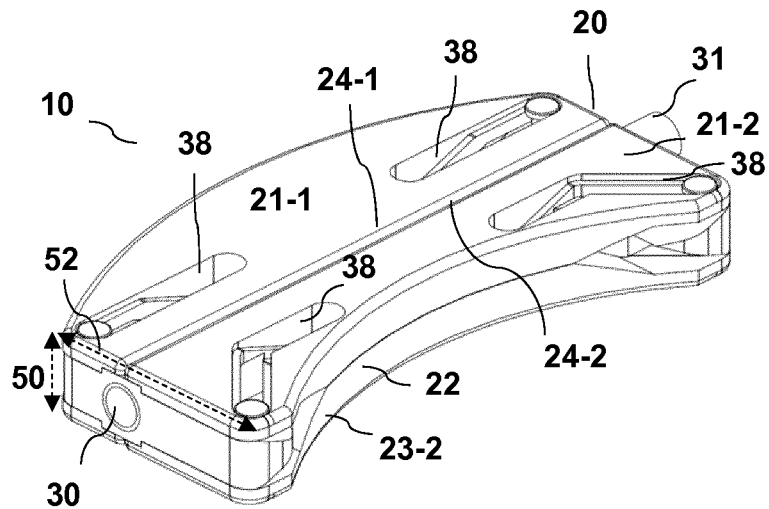
FIGS. 3a-3c depict a third embodiment of a placeholder according to the invention for spinal surgery in the closed state, in the open state and in the expanded, e.g., open and raised state.
Figure 3B:
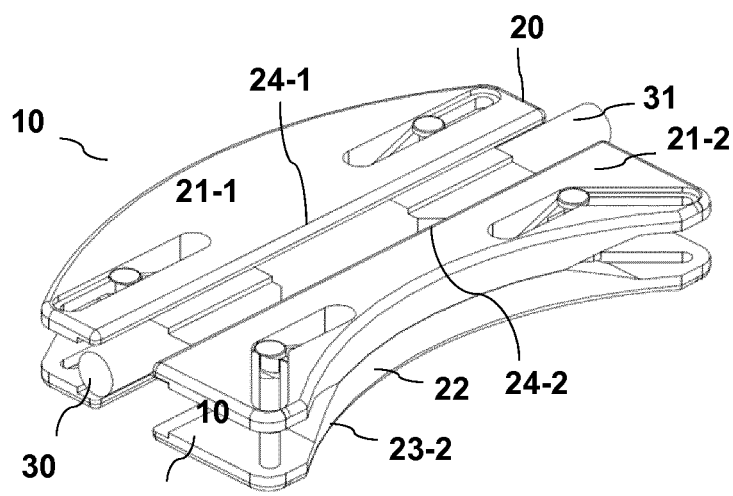
Figure 3C:
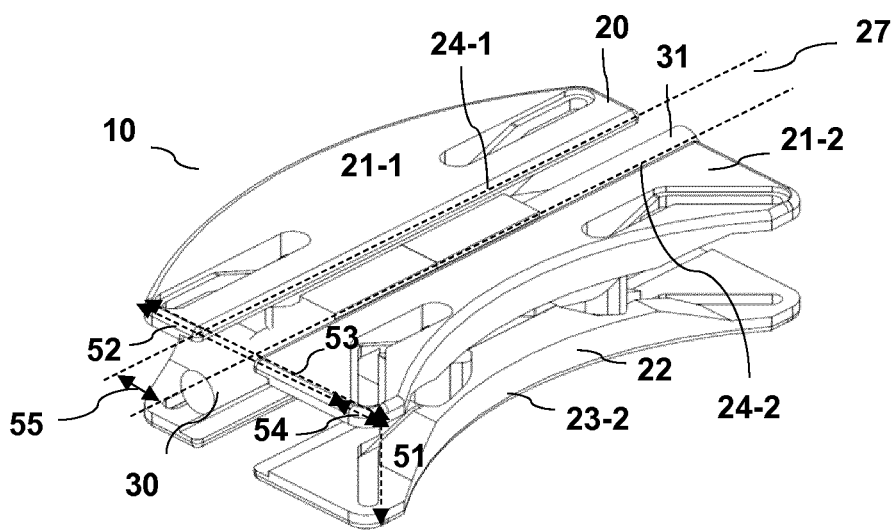

FIGS. 3a-3c show a third embodiment of the placeholder 10 according to the invention for spinal surgery in the closed state, the open state and in the expanded, e.g., open and raised state in each case in perspective views.

This third embodiment of the placeholder 10 according to the invention functions essentially as the second embodiment, and is thus also described at the corresponding points by the second embodiment. However, it has three special features, in which it differs from the second embodiment:

The placeholder 10 has no interengaging structure on the edge 24-1, 24-2, 25-1, 25-1, which the first 21-1, 23-1 and the second sub-surface 21-2, 23-2 of the upper 21 and the lower support surface 23 touch. This results in a lateral gap 27 in the course of the expansion, which can also be referred to herein as a central, medial or intermediate gap, the width 55 of which corresponds to the maximum drift amount 54 of the lateral extension of the upper 21 and lower support surfaces 23.

The elongated holes 38, 39, in which the mushroom heads used as guide elements, which are arranged on the wedge-shaped spacer elements, have a shape such that initially a linear change in the lateral extension takes place up to a maximum drift amount 54, during which a linear change in the lateral position of the sub-surfaces of the respective support surfaces and thus of the lateral extension of the placeholder is made, but then furthermore a linear change in the vertical distance or the vertical stroke takes place, while the lateral extension remains constant: Both the change in the lateral extension and the change in the vertical distance take place linearly, but offset with respect to one another. The algorithm of this sequence is coded in the formation of the elongated holes.

The placeholder 10 has a kidney-shaped form, therefore is particularly suitable for implantation on an arcuate implantation path.

Figure 4:
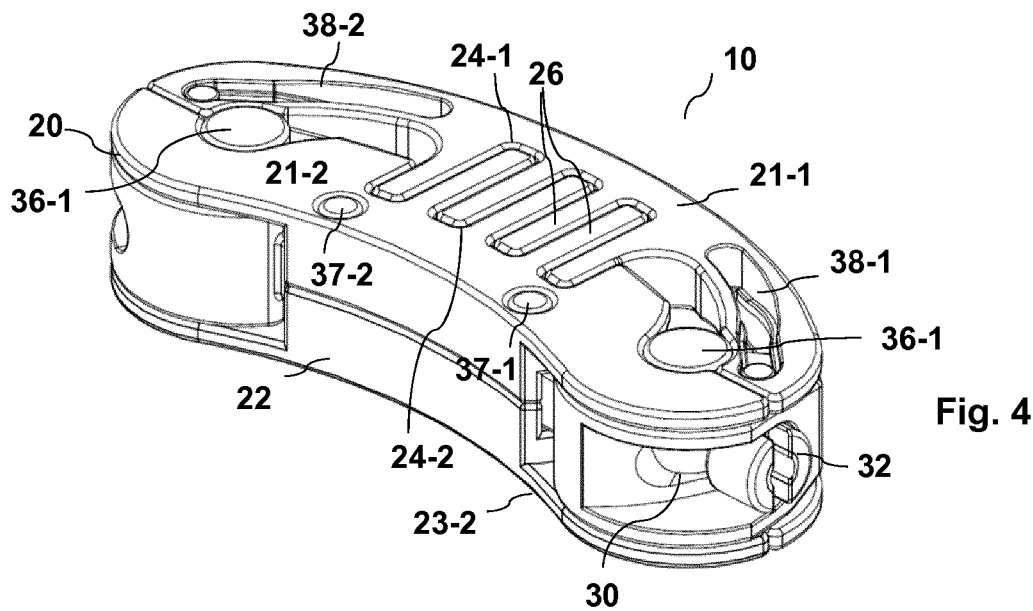
FIG. 4 depicts a fourth embodiment of a placeholder according to the invention for spinal surgery in the closed state.
Figure 5A:
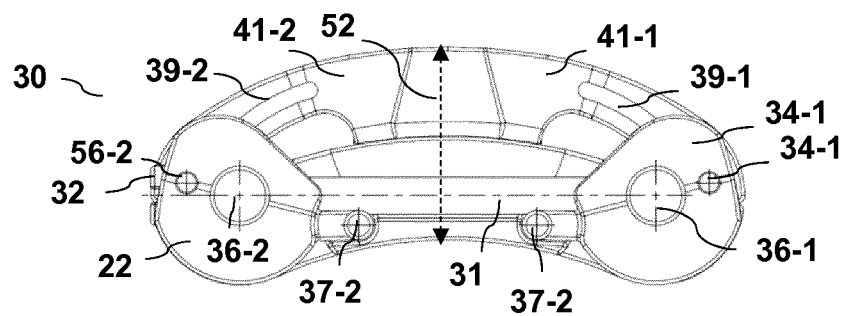
FIGS. 5a-5c depict an interior view of the fourth embodiment of a placeholder according to the invention in the closed state, in the open state and in the expanded, e.g., open and raised state.
Figure 5B:
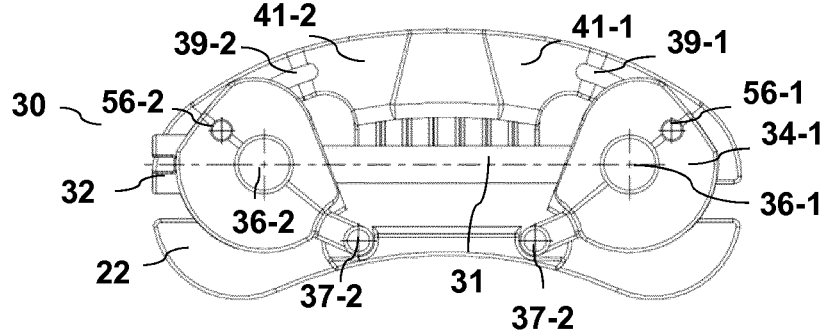
Figure 5C:
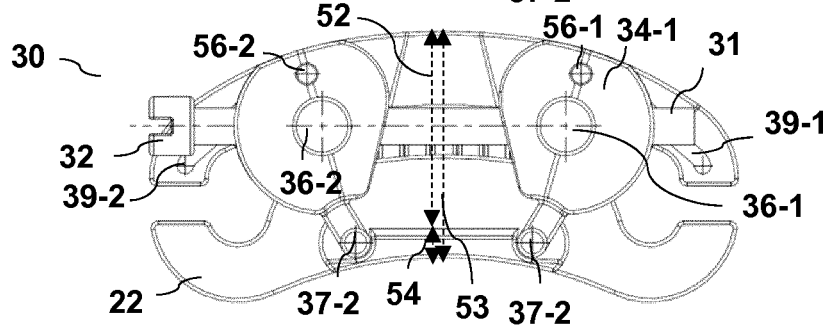

In FIG. 4, a fourth embodiment of a placeholder 10 according to the invention for spinal surgery is shown in the closed state, of which FIGS. 5a-5c show an interior view in the closed state, in the open state and in the expanded, e.g., open and raised state.

The fourth embodiment of the placeholder according to the invention also comprises an upper support 20 with an upper support surface 21 and a lower support 22 with a lower support surface 23, the relative position of which with respect to one another can be changed, wherein the upper 21 and the lower support surface 23 in each case has a first 21-1, 23-1 and a second sub-surface 21-2, 23-2, which touch an edge 24-1, 24-2, 25-1, 25-1 in a closed state of the placeholder 10. The placeholder also comprises an expansion device 30, with which the support surfaces 21, 23 can be changed with respect to one another in their lateral extension through lateral drifting apart of the first 21-1, 23-1 and second sub-surface 21-2, 23-2 of the support surfaces 21, 23 up to a maximum drift amount 54 between a minimum lateral extension 52 and a maximum lateral extension 53 as well as in their vertical distance between a minimum height 50 and a maximum height 51 of the placeholder 10, so that the placeholder 10 can be adjusted between a closed and an expanded state.

And also in this fourth embodiment of the placeholder 10 according to the invention, the first 21-1, 23-1 and the second sub-surface 21-2, 23-2 of the upper 21 and of the lower support surface 23 at the edge 24-1, 24-2, 25-1, 25-1, at which they touch in the closed state, have an interengaging structure 26 in the form of interengaging teeth. Said structure is designed in such a way, that in the event of an expansion, it permits a lateral drifting apart of the first 21-1, 23-1 and second sub-surface 21-2, 23-2, and, in the expanded state, a lateral gap running perpendicular to the direction of lateral drifting apart through the upper 21 and the lower support surface 23 has a gap width, which is smaller than the maximum drift amount: In this case, the gap width in the central region of the contact surfaces 21, 23 is zero, only in the edge regions of the support surfaces does a real lateral gap still occur.

The expansion device 30 of the fourth embodiment of the placeholder 10 according to the invention further comprises a movable spacer element 34, which differs from the previously described spacer elements: It is mounted in a position on the spacer element 34 so as to be laterally rotatable about a movable axis 36, which can be displaced along the screw spindle 31 by means of a threaded nut integrated into the movable axis 36 and running on a thread 33 of the screw spindle 31, wherein the movable axis 36 is arranged running indirectly in an upper elongated hole 38 in the first sub-surface 21-1 of the upper support 20 and in a lower elongated hole 39 in the first partial surface 23-1 of the lower support 22. The spacer element is furthermore laterally rotatable about a fixed axis 37, which is mounted in the second sub-surface 21-2 of the upper support 20 and in the second sub-surface 23-2 of the lower support 22 in a laterally positionally invariable manner.

In addition, the spacer element is mounted on a first and/or a second end in a freely sliding manner on an upper three-dimensional sliding surface 40 below the first 21-1 and/or the second sub-surface 21-2 of the upper support 20 and on a lower three-dimensional sliding surface 41 above the first 23-1 and/or second sub-surface 23-2 of the lower support 22, wherein the upper three-dimensional sliding surface 40 and the lower three-dimensional sliding surface 41 are shaped relative to each other, so that for each angle of rotation of the spacer element 34 about the fixed axis 37, the first and/or second end of the spacer element 34 assumes a defined position on the upper 40 as well as on the lower three-dimensional sliding surface 41, the absolute position of which and the corresponding position of the movable axis 36 in the correspondingly shaped elongated holes 38, 39 determines the lateral extension of the placeholder 10 and the distance between the upper 40 and the lower three-dimensional sliding surface 41 relative to one another in the closed state determines the height of the placeholder 10.

In this fourth embodiment of the placeholder 10 according to the invention, the expansion device 30 thereby comprises a first spacer element 34-1, which uses the first half 31-1 of the screw spindle, and a second spacer element 34-2, which uses the second half 31-2 of the screw spindle 31. First 40-1, 41-1 or second upper and lower three-dimensional sliding surfaces 40-2, 41-2, in each case first or second movable axis 36-1, 36-2 and first or second fixed axis 37-1, 37-2 and corresponding upper 38-1, 38-2 and lower elongated holes 39-1, 39-2 are associated with first 34-1 and second spacer element 34-2.

The fourth embodiment of the placeholder 10 according to the invention, in turn, has a kidney-shaped form, is therefore particularly suitable for implantation on an arcuate implantation path. After its application to its site of action, this placeholder can then be expanded operating in a mirror-image manner with the spacer elements, which is very advantageous, if it has been brought, for example, into a central position instead of the intervertebral disc between two vertebral bodies and, during expansion, a uniform pressure is to be exerted over the entire central region.

The position and shape of the elongated holes and of the three-dimensional sliding surfaces of the fourth embodiment are designed in such a way that a non-linear lateral expansion and a linear vertical expansion are carried out.

FIGS. 6a-6c show a fifth embodiment of a placeholder 10 according to the invention for spinal surgery in the closed state, in the open state and in the expanded, e.g., open and raised state—again in a perspective view, while in FIGS. 7a-7c an interior view of the fifth embodiment of a placeholder 10 according to the invention is shown in the closed state, in the open state and in the expanded, e.g., open and raised state—in the same perspective view.

For this fifth embodiment of the placeholder 10 according to the invention, what has been stated for the fourth embodiment applies, but differs from this fourth embodiment in the following special features:

The spacer element 34 or the spacer elements 34-1, 34-2 are realised by means of cams, the ends of the cams are mounted in a sliding manner on three-dimensional sliding surfaces 41-1, 41-2.

The first 21-1, 23-1 and the second sub-surface 21-2, 23-2 of the upper 21 and of the lower support surface 23 have an interengaging structure 26 in the form of interengaging teeth on the edge 24-1, 24-2, 25-1, 25-1 at which they touch in the closed state. This structure continues—partially periodically, partially at irregular intervals over the entire length of the upper 21 and also of the lower support surface 23, and is designed in such a way that, during an expansion, it permits lateral drifting apart of the respective first 21-1, 23-1 and second sub-surfaces 21-2, 23-2. The structure of the interengaging teeth, however, extends over the entire lateral width of the placeholder 10 in the closed state, so that even in the expanded state there is no lateral gap, therefore the gap width of an imaginary lateral gap perpendicular to the direction of lateral drifting apart is equal to zero. Furthermore: The upper 20 and the lower support 22 are shaped in such a way, that the interengaging tooth structure 26 of the first sub-surface 21-1, 23-1 can slide together in a more stable and secure manner on a support structure 44 in the part of the support 20, 22 associated with the second sub-surface 21-2, 23-2 and the interengaging tooth structure 26 of the second sub-surface 21-2, 23-2 on a part of the support 20, 22 associated with the first sub-surface 21-1, 23-1 during the lateral drifting apart during the expansion of the placeholder 10.

The fifth embodiment of the placeholder 10 according to the invention has, in its top view, a basic shape, which is cuboid in the broadest sense, even if with rounded corners. It is therefore particularly suitable for a straight implantation path 70, but its use due to its rounded corners is also not excluded on an arcuate implantation path 70.

The screw spindle 31 used as a central drive element is brought into an edge region in any state of the placeholder 10, which facilitates actuation of the screw spindle 31 by means of a tool engaging in the screw head 32 with corresponding placement of the placeholder 10 at its site of action ventrally in front of the vertebral canal of the spinal column.

If one considers the inner workings of the fifth embodiment of the placeholder 10 according to the invention more precisely, it can be seen that the position of the cams 34-1, 34-2 relative to the axis of the screw spindle 31 in the closed state of the placeholder 10 is approximately 20°, in the initially only laterally open state of the placeholder approximately 70° and in the expanded, that is, open and raised state, approximately 100°. The change in the vertical distance and thus the vertical stroke therefore takes place relatively quickly at the end of the expansion of the placeholder when the cams 34-1, 34-2 slide over a short but steeply rising region of the three-dimensional sliding surfaces 40-1, 40-2, 41-1, 41-2.

Figure 8A:
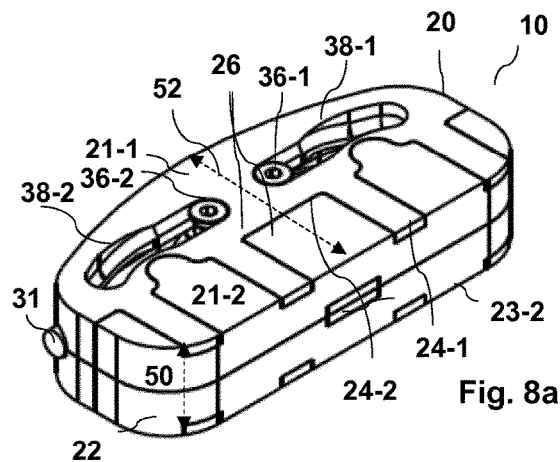
FIGS. 8a-8c depict a sixth embodiment of a placeholder according to the invention for spinal surgery in the closed state, in the open state and in the expanded, e.g., open and raised state.
Figure 9A:
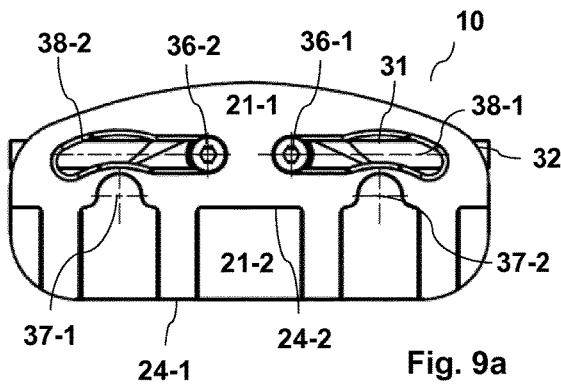
FIGS. 9a-9c depict a top view of the sixth embodiment of a placeholder according to the invention in the closed state, in the open state and in the expanded, e.g., open and raised state.
Figure 8B:
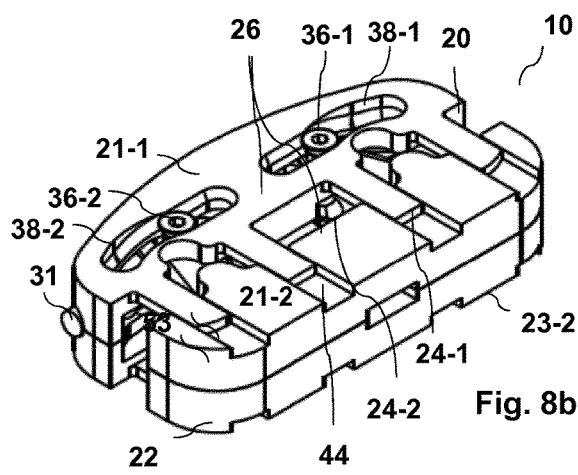
Figure 9B:
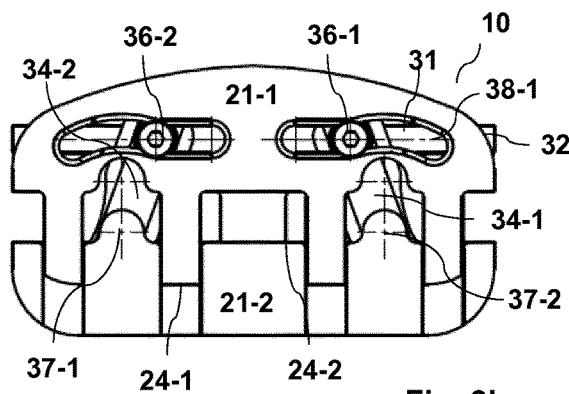
Figure 8C:
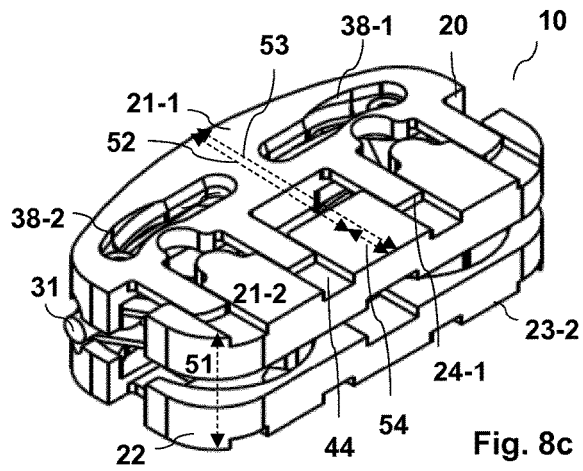
Figure 9C:
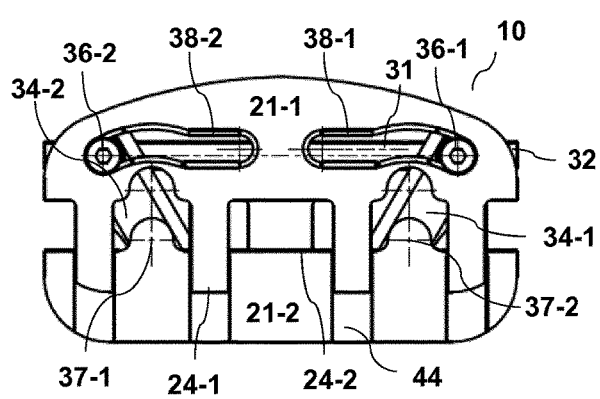

In FIGS. 8a-8c, a sixth embodiment of a placeholder 10 according to the invention for spinal surgery is shown in the closed state, in the open state and in the expanded, e.g., open and raised state, in each case in a perspective view, in FIGS. 9a-9c a top view of the sixth embodiment of a placeholder 10 according to the invention is shown in the closed state, in the opened state and in the expanded, e.g., open and raised state; FIG. 10 an exploded view of the sixth embodiment of a placeholder 10 according to the invention, and in FIGS. 11a-11c an interior view of the sixth embodiment of a placeholder 10 according to the invention is shown in the closed state, in the opened state and in the expanded, e.g., open and raised state.

This sixth embodiment of the placeholder 10 according to the invention is described with the fifth embodiment except for the following special features:

The first 21-1, 23-1 and the second sub-surface 21-2, 23-2 of the upper 21 and of the lower support surface 23 have an irregularly interengaging structure 26 over the entire length of the upper 21 and of the lower support surface 23 at the edge 24-1, 24-2, 25-1, 25-1, at which they touch in the closed state. This structure is also designed in such a way that it enables a lateral drifting apart of the respective first 21-1, 23-1 and second sub-surfaces 21-2, 23-2 during an expansion. Although the interengaging structure 26 does not extend over the entire width of the support surfaces 21, 23 in the closed state of the placeholder 10, there is also no lateral gap here in the expanded state, the gap width of an imaginary lateral gap perpendicular to the direction of the lateral drifting apart is therefore equal to zero. And here, too, the upper 20 and the lower support 22 are shaped in such a way, that the interengaging structure 26 of the first sub-surface 21-1, 23-1 can slide together in a more stable and secure manner on a support structure 44 in the part of the support 20, 22 associated with the second sub-surface 21-2, 23-2 and the interengaging tooth structure 26 of the second sub-surface 21-2, 23-2 on a support structure 44 in the part of the support 20, 22 associated with the first sub-surface 21-1, 23-1 during the lateral drifting apart during the expansion of the placeholder 10.

The sixth embodiment of the placeholder 10 according to the invention has, in its top view, a kidney-shaped or arcuate shape on one side, while the shape on the other side is, in the broadest sense, cuboid with rounded corners. It is therefore particularly suitable for an arcuate implantation path 70, since in particular the otherwise "abutting" side of the placeholder 10 is of arcuate configuration, but its use is also not excluded on a straight implantation path 70.

Both in the exploded view of FIG. 10 and in the views of the inner workings of FIGS. 11a-11c of the sixth embodiment, the two-part design of the screw spindle 31 with a right-hand thread on its first half 31-1 and a left-hand thread on its second half 31-2 can be seen very well.

The screw spindle 31 of this sixth embodiment of a placeholder according to the invention has a guide structure 45 between its first 31-1 and second half 31-2, which is mounted rotatably, but not laterally displaceably, in its position in a retaining element 46, wherein the retaining element 46 is mounted movably, in particular vertically movably, but in turn is not laterally displaceable in its position in the upper 20 and in the lower support 22, and thus centres the expansion device with respect to the supports.

Figure 14:
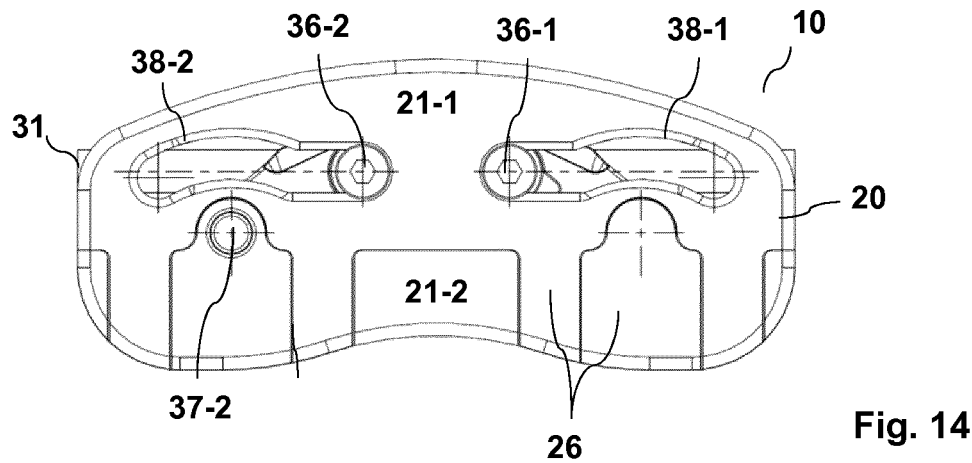
FIG. 14 depicts a top view of the seventh embodiment of a placeholder according to the invention.
Figure 15A:
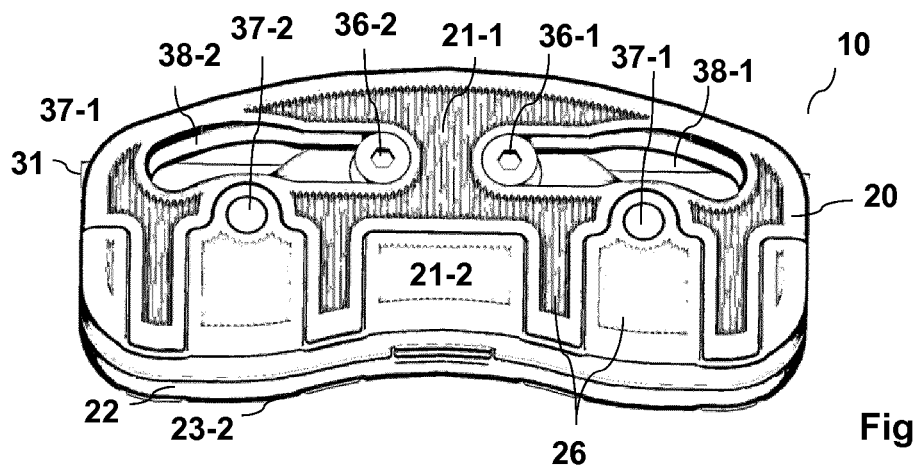
FIGS. 15a and 15b depict a perspective view of the seventh embodiment of a placeholder according to the invention.
Figure 15B:
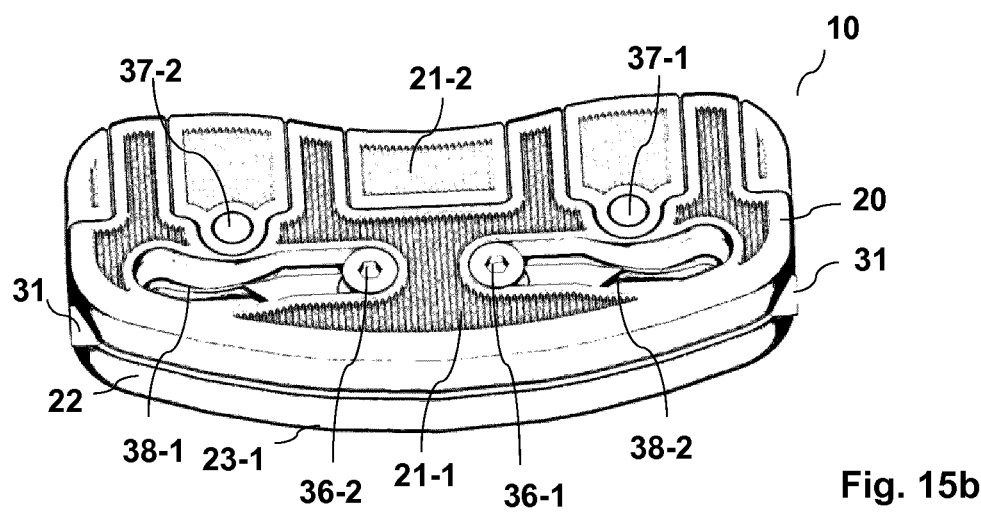

FIGS. 12a-12c finally show a seventh embodiment of a placeholder 10 according to the invention for spinal surgery in the closed state, in the open state and in the expanded, e.g., open and raised state, in a perspective view. In FIG. 14, a top view and in FIGS. 15a and 15b two further perspective views of the seventh embodiment of a placeholder 10 according to the invention are shown in the closed state—designed more plastically in comparison with FIGS. 12a-12c.

Here too, for the description of the seventh embodiment, reference is first made to the description of the sixth embodiment of the placeholder 10 according to the invention, from which it differs in the following points:

The seventh embodiment of the placeholder 10 according to the invention again has a purely kidney-shaped form and is consequently particularly suitable for implantation on an arcuate implantation path 70.

As can be seen in the interior views of the seventh embodiment of a placeholder according to the invention of FIGS. 13a to 13d in the closed state in a position of the cams 34-1, 34-2 serving as spacer elements, relative to the axis of the screw spindle 31 of approximately 25°, in the open state in a position of the cams 34-1, 34-2 relative to the axis of the screw spindle 31 of approximately 65°, in the open and partially raised state in the case of a position of the cams 34-1, 34-2 relative to the axis of the screw spindle 31 of approximately 110° and in the expanded state, e.g. completely open and raised, in the position of the cams 34-1, 34-2 relative to the axis of the screw spindle 31 of approximately 120°, this embodiment is that which combines the various features according to the invention for the greatest benefit:

In addition to the interengaging structure 26 of the sub-surfaces 21-1, 23-1, 21-2, 23-2 with the support of support structures 44 in the supports 20, 22 of the respective other sub-surface 21-2, 23-2, 21-1, 23-1 and associated therewith a secure sliding during the change in the lateral extension and prevention of a continuous lateral gap 27, a kidney-shaped form for use in an arcuate implantation path 70, an arrangement of the screw spindle 31 in the edge region of the placeholder 10 and the use of two spacer elements 34-1, 34-2 in the form of cams, which operate in a mirror-image manner, wherein the screw spindle 31 in turn has a guide structure 45 between its first 31-1 and second half 31-2, which can be rotated in a retaining element 46, but is not laterally displaceably mounted in its position, and the retaining element 46 is mounted only vertically movably in the upper 20 and in the lower support 22, this seventh embodiment of the placeholder 10 according to the invention shows an expansion device 30, which performs the change in the lateral extension and the vertical distance in two movement courses, which are independent of one another and freely defined—and varied several times in the course of the expansion—by means of a single drive: This is done with non-linear, curved sliding surfaces or "shift surfaces", which resemble articulation surfaces of the vertebral joints, and correspondingly shaped elongated holes which are used as sliding holes.

Figure 16A:
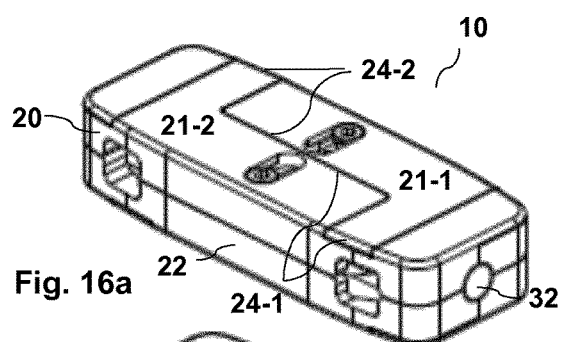
FIGS. 16a-16c depict an eighth embodiment of a placeholder according to the invention for spinal surgery in the closed state, in the open state and in the expanded, e.g., open and raised state, in a perspective view.
Figure 17A:
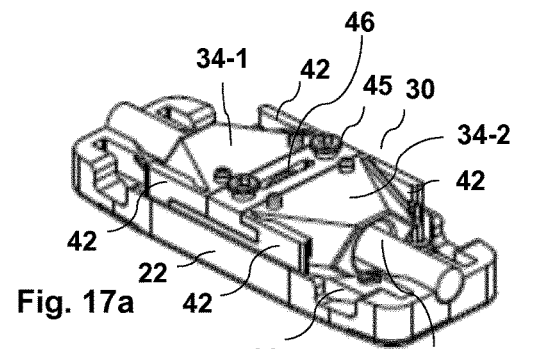
FIGS. 17a-17c depict an interior view of the eighth embodiment of a placeholder according to the invention in the closed state, in the open state, and in the expanded, e.g., completely open and raised state, in a perspective view.
Figure 16B:
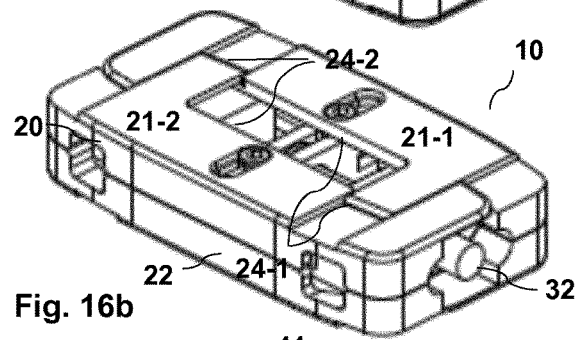
Figure 17B:
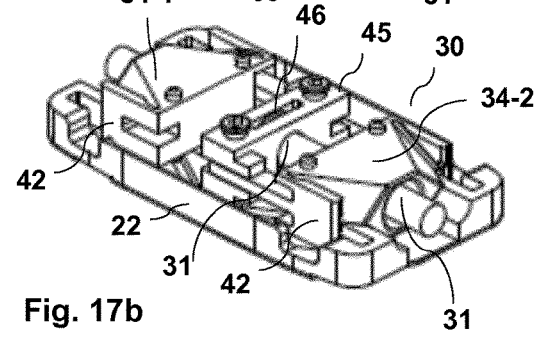
Figure 16C:
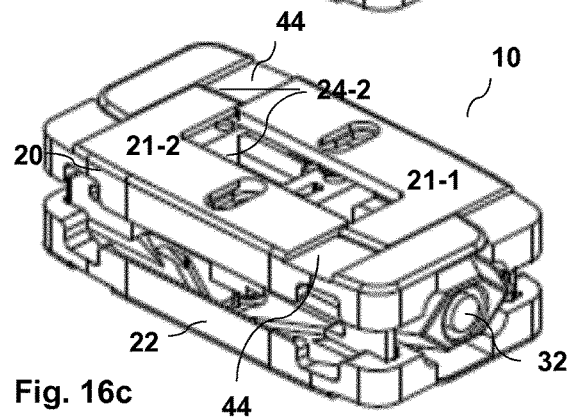
Figure 17C:
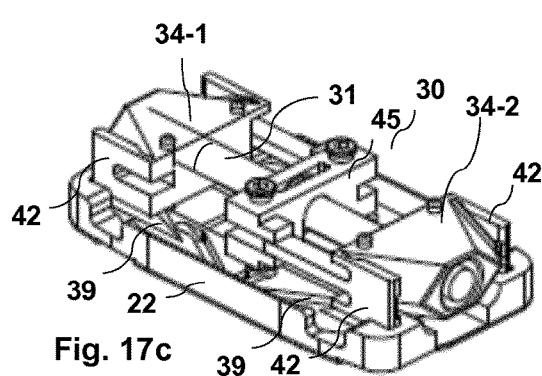
Figure 18A:
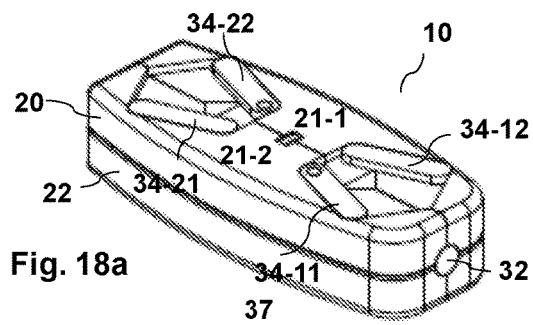
FIGS. 18a-18d depict a ninth embodiment of a placeholder according to the invention for spinal surgery in the closed state, in the opened state, in the expanded, e.g., open and raised state, and in the expanded and locked state in a perspective view.
Figure 19A:
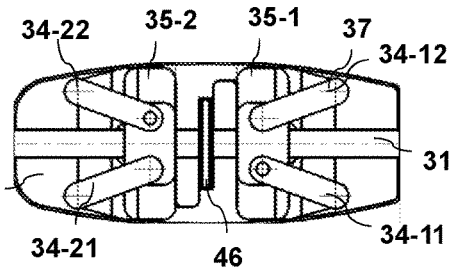
FIGS. 19a to 19d depict an interior view of the ninth embodiment of a placeholder according to the invention in the closed state, in the opened state, in the expanded, e.g., open and raised state, and in the expanded and locked state in a top view.
Figure 18B:
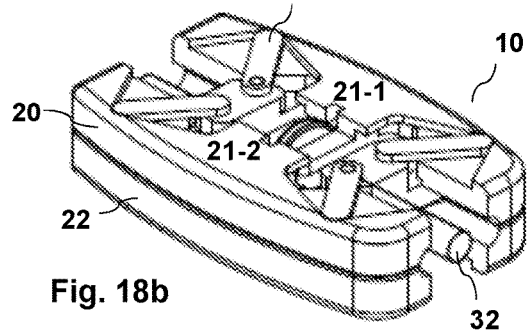
Figure 19B:
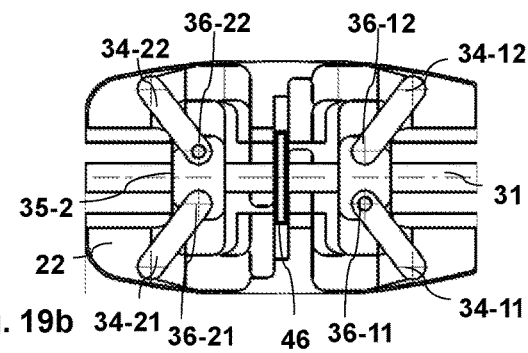
Figure 18C:
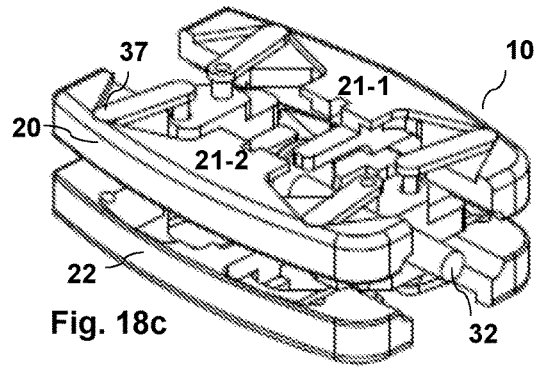
Figure 19C:
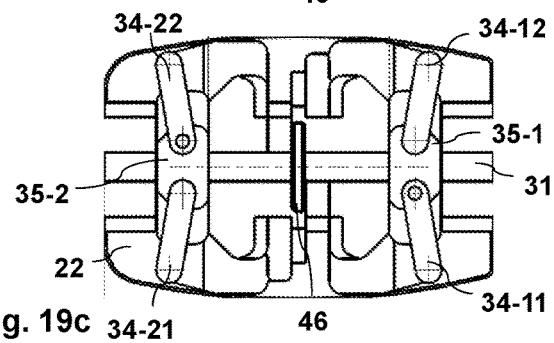
Figure 18D:
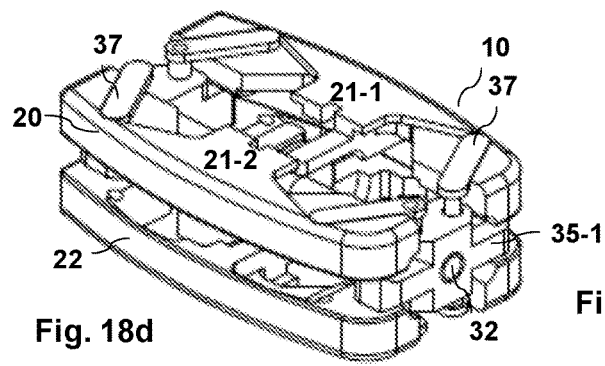
Figure 19D:
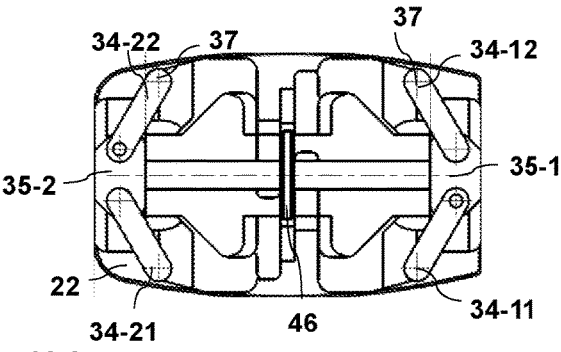
Figure 20A:
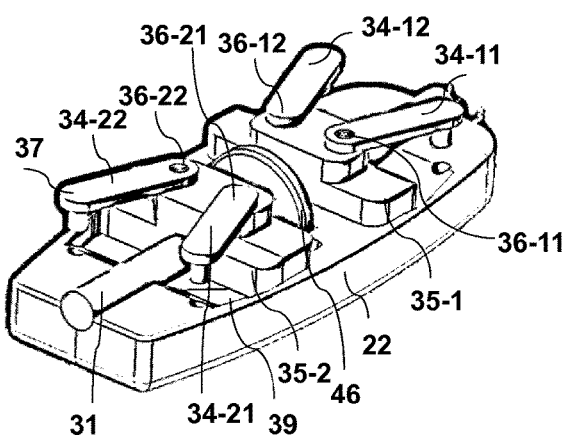
FIGS. 20a-20d depict an interior view of the ninth embodiment of a placeholder according to the invention in the closed state, in the opened state, in the expanded, e.g., open and raised state, and in the expanded and locked state in a perspective view.
Figure 20B:
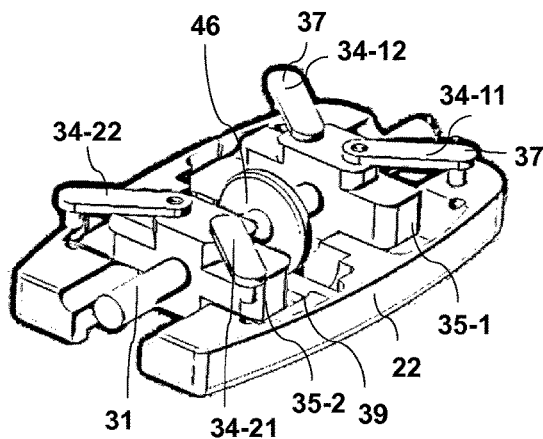
Figure 20C:
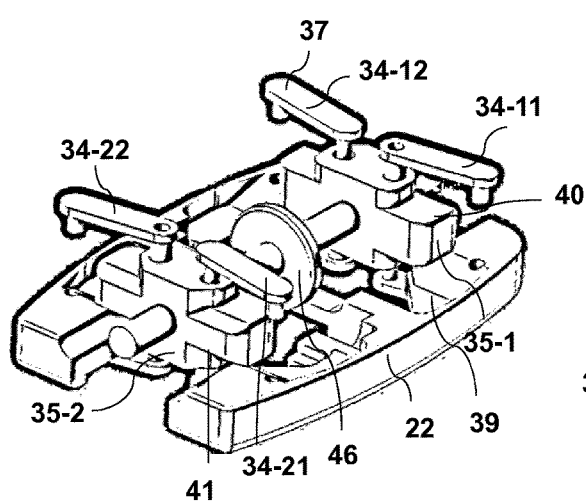
Figure 20D:
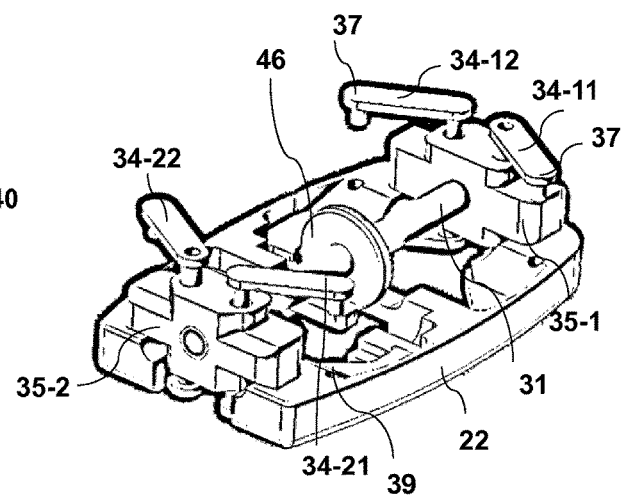

In FIGS. 16a-16c, an eighth embodiment of a placeholder 10 according to the invention for spinal surgery is shown in the closed state, in the open state and in the expanded, e.g., open and raised state, in a perspective view. FIGS. 17a-17c show a corresponding and likewise perspective internal view of the eighth embodiment.

This placeholder 10 in turn comprises an upper support 20 with an upper support surface 21 and a lower support 22 with a lower support surface 23, the relative position of which can be varied with respect to one another, wherein the upper 21 and the lower support surface 23 in each case has a first 21-1, 23-1 and a second sub-surface 21-2, 23-2, which in a closed state of the placeholder 10 touch an edge 24-1, 24-2, 25-1, 25-1. The placeholder also comprises an expansion device 30, by means of which the support surfaces 21, 23 can be changed in their lateral extension by lateral drifting apart of the first 21-1, 23-1 and second sub-surfaces 21-2, 23-2 as well as in their vertical distance between the upper 21 and lower support surfaces 23, so that the placeholder 10 can be adjusted between a closed and an expanded state.

This eighth embodiment of the placeholder according to the invention in turn pursues a wedge principle, which is described in the first three embodiments, but in modified form: The movable spacer elements 34-1, 34-2 in turn have a wedge shape which, however, is not responsible solely for changing the vertical distance between the upper 20 and the lower support 22. Rather, the movable spacer elements 34-1, 34-2 comprise guide elements 42 for this purpose on their side surfaces. In turn, these guide elements slide in upper and lower guide sliding surfaces 38, 39, which are arranged below the upper sub-surfaces 21-1, 21-2 of the upper support 20 as well as on the lower sub-surfaces 23-1, 23-2 of the lower support 22 (e.g., directed inwardly and in a view, that reflects "on" an outer position, then again "below" the lower sub-surfaces 23-1, 23-2), so that the guide elements 42 arranged on the spacer elements 34-1, 34-2 can slide in these upper and lower guide sliding surfaces 38, 39.

In contrast to the upper and lower preferably three-dimensional sliding surfaces 40, 41 mentioned in other embodiments at approximately similar positions—the guide sliding surfaces 38, 39 are thereby designed in such a way that they assume the lateral positioning in its entirety, e.g., are very sharply defined in terms of their formation, and exactly reflect both the course of the lateral and the vertical movements. The expansion device 30 of this eighth embodiment can in this way carry out the change in the lateral extension and of the vertical distance in two movement courses, which are independent and freely definable, but by means of a single drive: Lateral and vertical courses can be coded freely into the guide sliding surfaces 38, 39 by corresponding shaping. Further (sliding) surfaces of the spacer elements 34-1, 34-2 support this course of movement.

In contrast to the wedge-shaped spacer elements of the first three embodiments—the spacer elements 34-1, 34-2 move outward on a screw spindle 31 from the inside (in order to realise a closed state) to the outside, e.g., away from one another, in order to realise an expanded state. In the closed state, the two wedge-shaped spacer elements 34-1, 34-2 rest on a guide structure 45, which is likewise arranged on the screw spindle 31, in which in in turn a retaining element 46 on the screw spindle 31 provides for correct positioning of the guide structure 45 relative to the screw spindle and structures moving in lateral elongated holes in the sub-surfaces 21-1, 21-2, 23-1, 23-2 provide for correct positioning of the guide structure 45 relative to the upper 20 and lower supports 22.

Also, in this eighth embodiment of the placeholder 10 according to the invention the first 21-1, 23-1 and the second sub-surface 21-2, 23-2 of the upper 21 and of the lower support surface 23 at the edge 24-1, 24-2, 25-1, 25-1, at which they touch in the closed state, have an interengaging structure with additional support structures 44. This interengaging structure is also designed in such a way that it permits a lateral drifting apart of the first 21-1, 23-1 and second sub-surfaces 21-2, 23-2 during expansion and, in the expanded state, a lateral gap 27 running perpendicular to the direction of lateral drifting apart through the upper 21 and the lower support surface 23 has a gap width 55, which is substantially smaller than the maximum drift amount 54—in the case of this eighth embodiment is virtually non-existent and thus zero. In the closed state of the placeholder 10, the interengaging structures of the first and second sub-surface of the upper and also of the lower support surfaces show an interengaging in accordance with the "key-lock principle" over the entire length of the placeholder, so that, in the closed state, the upper and also the lower support surface can be realised as in each case one continuous surface.

FIGS. 18a-18d show a ninth embodiment of a placeholder 10 according to the invention for spinal surgery in the closed state, in the opened state, in the expanded, e.g., open and raised state, and in the expanded and locked state in a perspective view. In FIGS. 19a-19d, an inside view of the ninth embodiment in the closed state, in the open state, in the expanded, e.g., open and raised state, and in the expanded and locked state is shown in a top view, and FIGS. 20a-20d show the interior view of the ninth embodiment in turn in a perspective view.

In this ninth embodiment, the number of movable spacer elements 34-11, 34-12, 34-21, 34-22 was doubled relative to the fourth to seventh embodiments. Each spacer element 34-11, 34-12, 34-21, 34-22 acts as a double pair, which is laterally rotatable about a fixed axis 37 in the first sub-surface 21-1, 23-1 of the upper 20 and lower support 22 or in the second sub-surface 21-2, 23-2 of the upper 20 and lower support 22, and about a movable axis 36-11, 36-12, 36-21, 36-22, which is arranged on a threaded nut 35-1, 35-2, wherein the threaded nut 35-1, 35-2 can slide on the screw spindle 31 from the inside (in order to realise a closed state) to the outside, away from one another, in order to realise an expanded state.

The position of the threaded nut 35-1, 35-2 on the screw spindle 31, via the angular position of the spacer-element double pairs 34-11, 34-12, 34-21, 34-22 correspondingly assumed for this position, thereby realises the lateral extension of the placeholder 10 and the special shape of the threaded nut 35-1, 35-2, which for this purpose has sliding surfaces 40, 41, which can slide on guide sliding surfaces 38, 39 in the first 21-1, 23-1 and second sub-surfaces 21-2, 23-2 of the upper 20 and lower supports 22, realises the vertical extension of the placeholder 10.

In turn, a retaining element 46 on the screw spindle 31 provided for the correct positioning of the entire expansion device 30 relative to the upper 20 and lower supports 22.

Figure 21A:
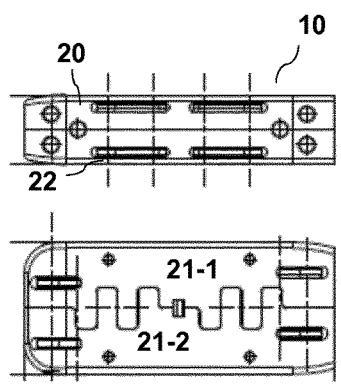
FIGS. 21a to 21c depict a tenth embodiment of a placeholder according to the invention for spinal surgery in the closed state, in the open state and in the expanded, e.g., open and raised state, in a side view and a top view.
Figure 21B:
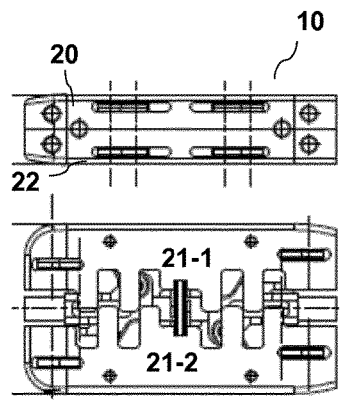
Figure 21C:
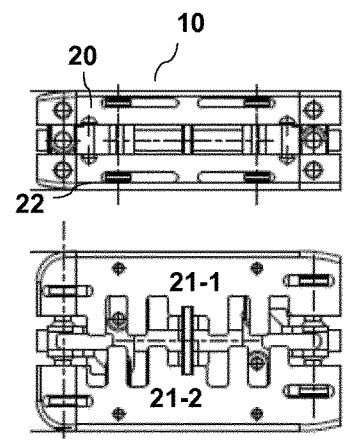
Figure 22A:
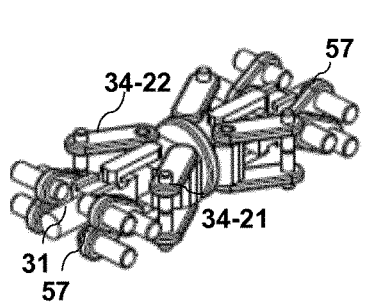
FIGS. 22a-22c depict an interior view of the tenth embodiment of a placeholder according to the invention in the closed state, in the open state and in the expanded, e.g., open and raised state, in a perspective view.
Figure 22B:
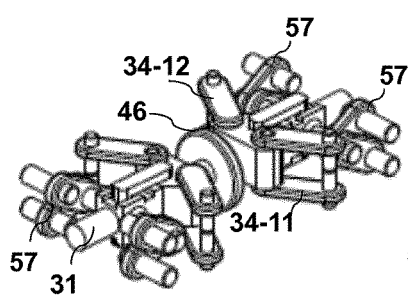
Figure 22C:
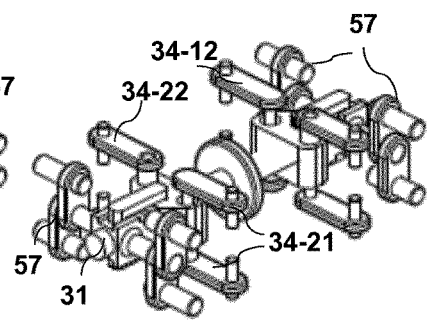
Figure 23A:
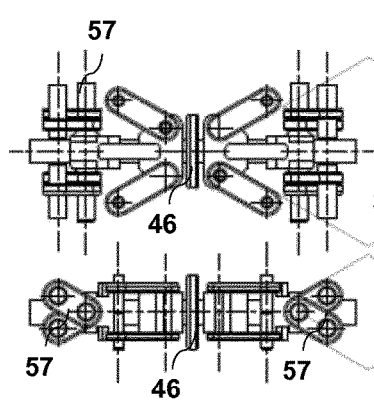
FIGS. 23a-23c depict an interior view of the tenth embodiment of a placeholder according to the invention in the closed state, in the open state and in the expanded, e.g., open and raised state, in a top view and a side view.
Figure 23B:
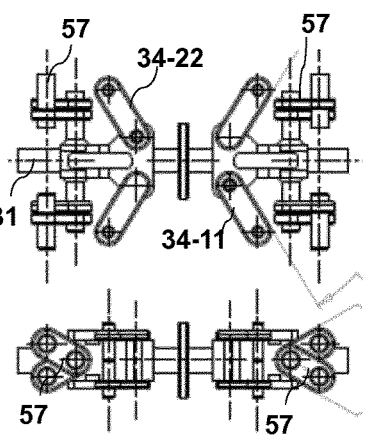
Figure 23C:
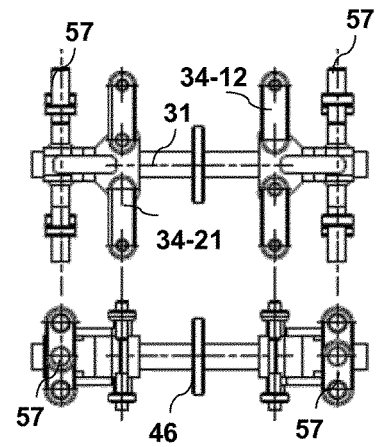
Figure 24A:
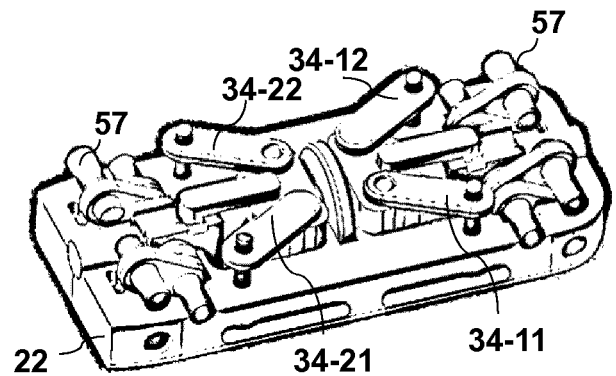
FIGS. 24a-24c depict a further interior view of the tenth embodiment of a placeholder according to the invention in the closed state, in the open state and in the expanded, e.g., open and raised state, in a perspective view.
Figure 24B:
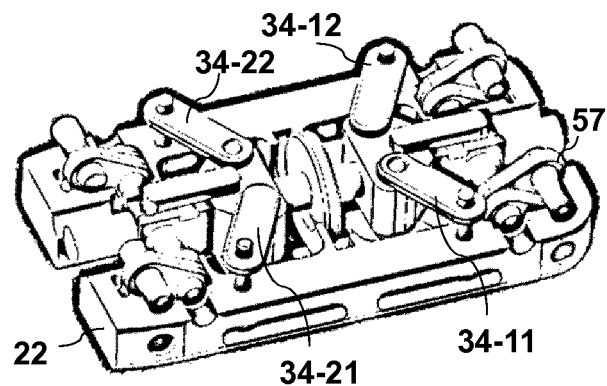
Figure 24C:
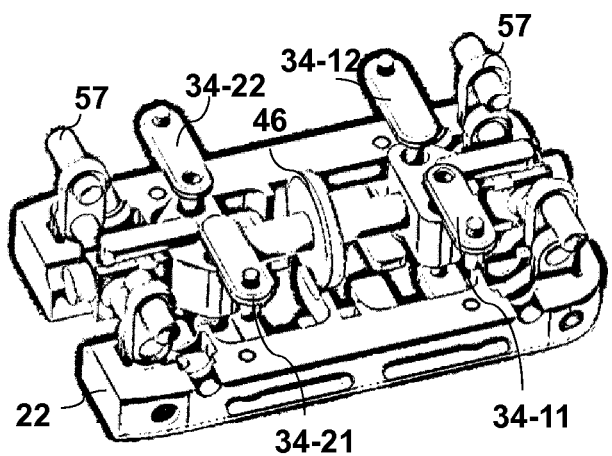

In FIGS. 21a to 21c, a tenth embodiment of a placeholder 10 according to the invention for spinal surgery is shown in the closed state, in the open state and in the expanded, e.g., open and raised state, in a side view and a top view, FIGS. 22a-22c show an interior view of the corresponding states of the tenth embodiment in a perspective view, FIGS. 23a-23c show an interior view of the corresponding state of the tenth embodiment in each case in a top view and a side view. In FIGS. 24a-24c a further interior view of the respective states of the tenth embodiment is shown in a perspective view.

This tenth embodiment corresponds in its construction first to the ninth embodiment. However, the vertical extension is not realised by a threaded nut 35-1, 35-2 comprising sliding surfaces, but rather the threaded nut 25-1, 25-2 here comprises in each case one toggle lever structure 57, which is located in corresponding guide structures on the undersides of the sub-surfaces 21-1, 21-2, 23-1, 23-2 of the upper 20 and lower 22 support: The position of the threaded nut 35-1, 35-2 on the screw spindle 31 thereby determines the position of the toggle lever structure 57, the opening angle of which and thus the vertical extension of the placeholder 10.

The tenth embodiment also again has an interengaging structure, which is designed in such a way that it permits a lateral drifting apart of the first 21-1, 23-1 and the second sub-surface 21-2, 23-2 during an expansion, and, in the expanded state, a lateral gap 27 between the first 21-1, 23-1 and second sub-surface 21-2, 23-2 running perpendicular to the direction of lateral drifting apart through the upper 21 and the lower support surface 23 has a gap width 55, which is substantially smaller than the maximum drift amount 54.

Figure 25A:
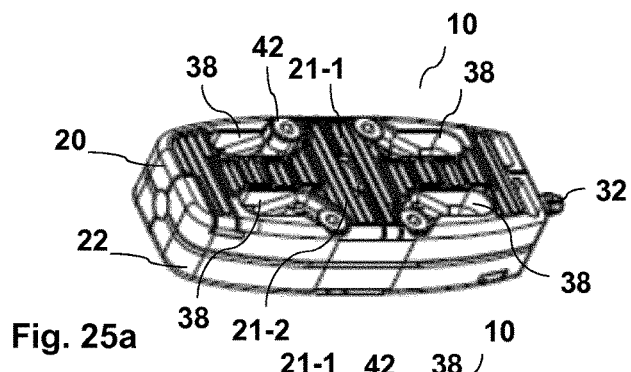
FIGS. 25a-25c depict an eleventh embodiment of a placeholder according to the invention for spinal surgery in the closed state, in the open state and in the expanded, e.g., open and raised state, in a perspective view.
Figure 25B:
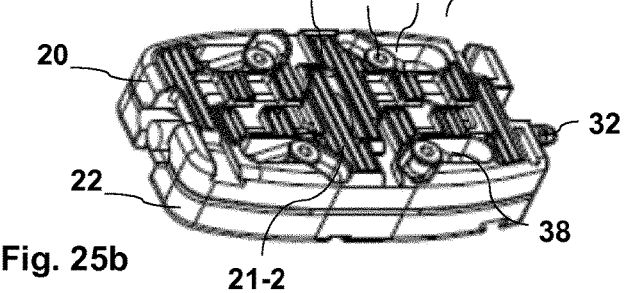
Figure 25C:
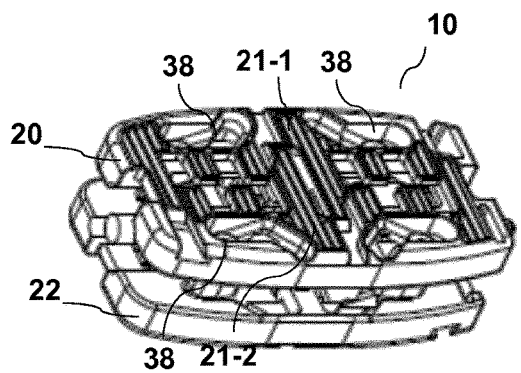
Figure 26A:
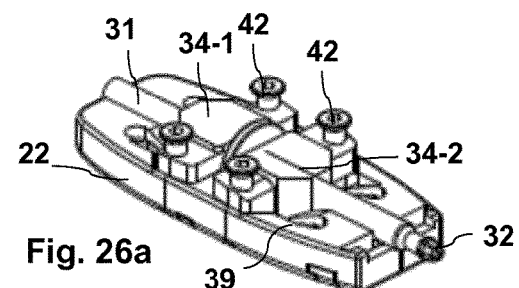
FIGS. 26a-26d depict an interior view of the eleventh embodiment of a placeholder according to the invention in the closed state, in the opened state, in the expanded, e.g., open and raised state, and in the expanded and locked state in a perspective view.
Figure 26B:
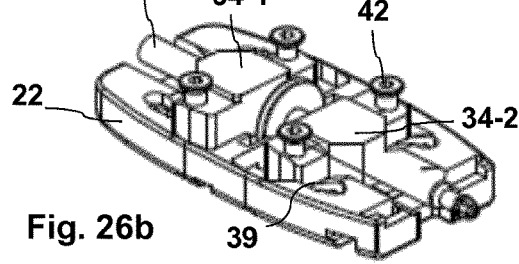
Figure 26C:
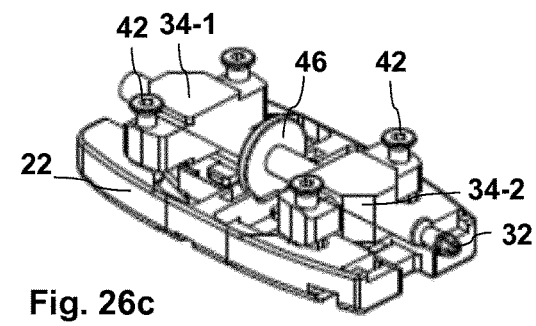
Figure 26D:
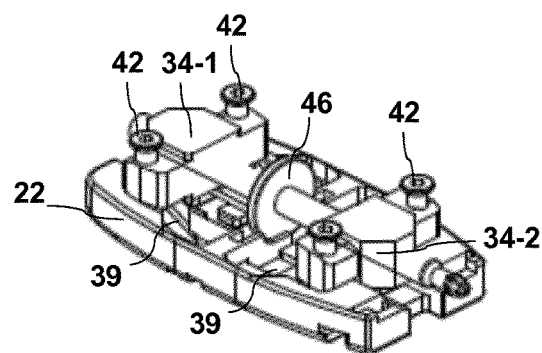

FIGS. 25a-25c show an eleventh embodiment of a placeholder 10 according to the invention for spinal surgery in the closed state, in the open state and in the expanded, e.g., open and raised state, in a perspective view. In FIGS. 26a-26d an interior view of the eleventh embodiment of a placeholder 10 according to the invention is shown in the closed state, in the opened state, in the expanded, e.g., open and raised state, and in the expanded and locked state in a perspective view.

This eleventh embodiment of a placeholder according to the invention in turn comprises movable spacer elements 34-1, 34-2, which move in opposite directions on the screw spindle 31: In a closed state of the placeholder 10, these spacer elements 34-1, 34-2 are adjacent in the interior of the placeholder 10 of a guide structure 45 with retaining element 46. During the expansion of the placeholder 10, these spacer elements 34-1, 34-2 move away from each other outwards. The eleventh embodiment thereby works according to a combination of a wedge principle with a guide through correspondingly shaped elongated holes 38, 39 (which determine the course of the lateral extension), in which guide elements 42 (here in a form of mushroom head bolts) of the spacer elements 34-1, 34-2 slide, and additional sliding surfaces 40, 41 below the sub-surfaces 21-1, 21-2, 23-1, 23-2 of the upper 20 and lower supports 22 and, optionally, also in the elongated holes 38, 39 themselves, by means of which the course of the vertical extension of the placeholder 10 is determined.

The eleventh embodiment also in turn has an interengaging structure of the first 21-1, 23-1 and second sub-surfaces 21-2, 23-2 of the upper 20 and lower support 22.

This eleventh embodiment of the placeholder 10 according to the invention shows an especially stable embodiment of such a placeholder.

All embodiments are designed in such a way that the placeholders can be implanted in a simple manner and then expanded accordingly, but they also allow the corresponding reversed path if this is necessary: They can be closed again in the opposite direction of rotation by a corresponding movement of the screw spindle 31 and can thus be removed again more easily from the spinal column of the patient.

Figure 27A:
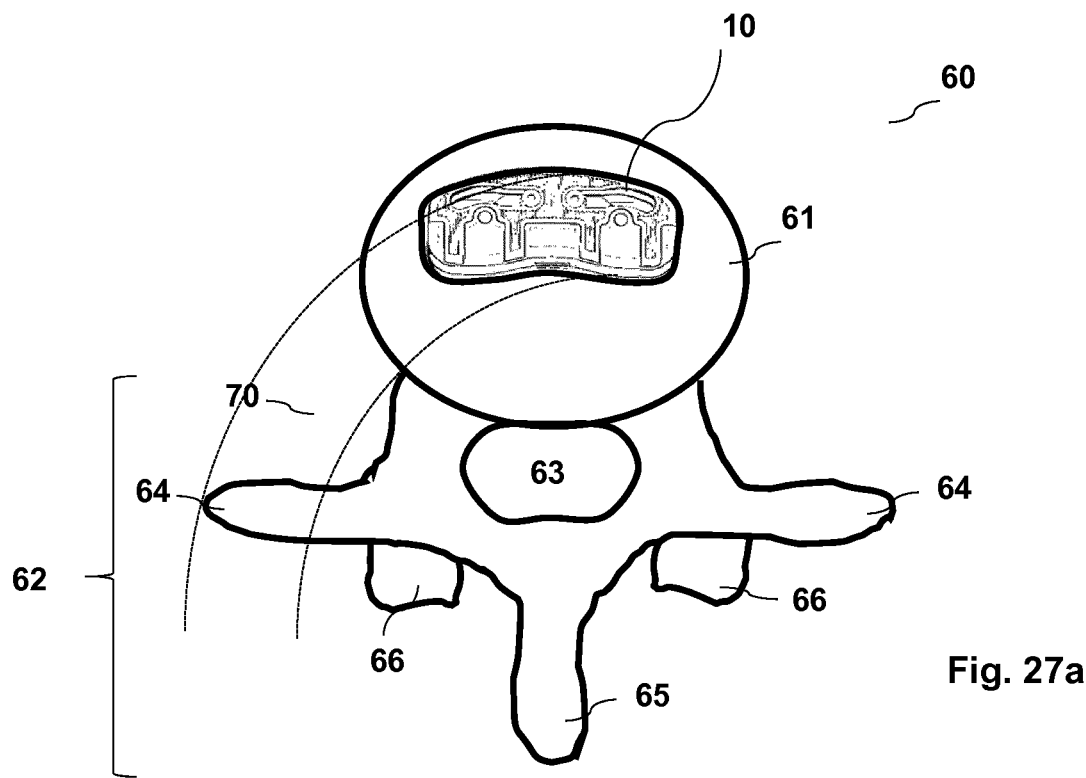
FIGS. 27a and 27b depict two variants of the implantation of the placeholder in a function as intervertebral body implant.
Figure 27B:
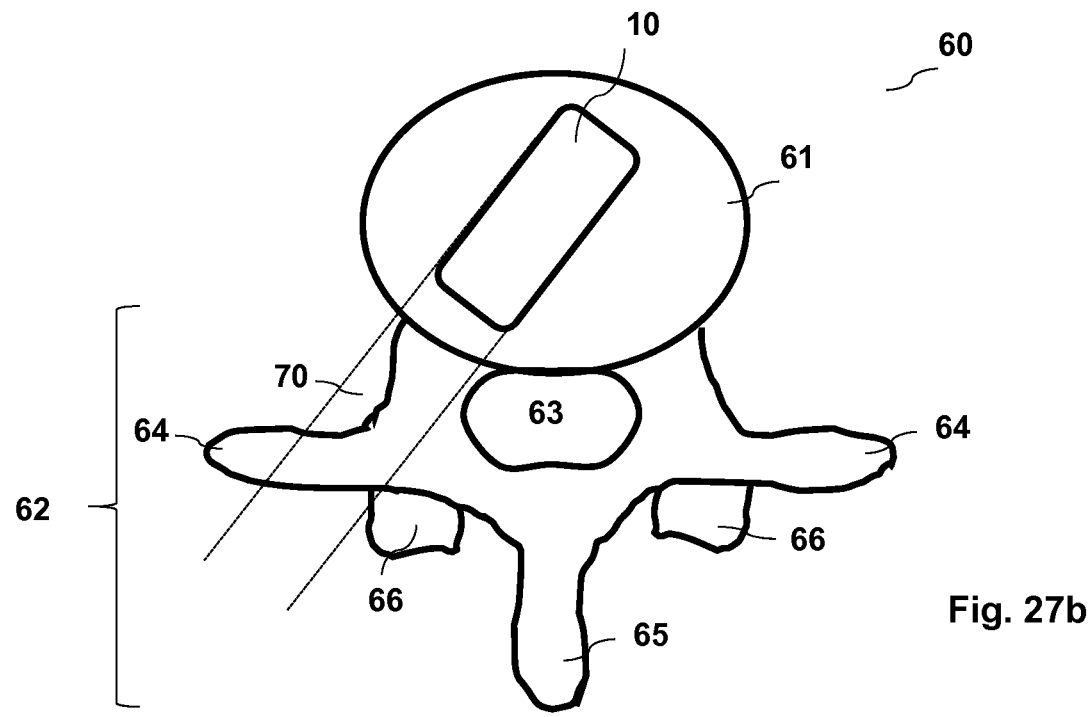

In FIGS. 27a and 27b two variants of the implantation of the placeholder are shown in a function as an intervertebral body implant:

FIG. 27a shows an arcuate implantation path 70 of a kidney-shaped placeholder 10 according to the invention into an intervertebral disc space between two vertebral bodies 61 of a vertebra 60 of the spinal column of a patient. In this case, a vertebra 60 has a vertebral body 61 and a vertebral arch 62, which in turn comprises transverse processes 64, a spinous process 65 and articular processes 66. In its interior, the vertebral canal 63 is located, which may in no case be damaged, since neural structures run there through. In contrast, in FIG. 27b a straight implantation path 70 of a placeholder 10 with a cuboid basic shape is shown in just this intervertebral disc space.

It can thereby easily be seen from the comparison of FIGS. 27a and 27b, that a minimally invasive, usable arcuate implantation path 70—as well as a minimally invasive, usable straight implantation path 70—passes through the vertebral arch 62, the arcuate implantation path 70 of FIG. 27a, however, relatively largely avoids the vertebral canal 63, while a straight implantation path 70, as shown in FIG. 27b, runs dangerously close along the vertebral canal 63.

In addition, the kidney-shaped placeholder 10, which has been implanted via the arcuate implantation path 70, is to be introduced ventrally very slightly symmetrically into the intervertebral disc space, while a straight implantation path 70 leads to a non-symmetrical position of the placeholder 10 in the intervertebral disc space.

FIG. 27a also makes clear once again, that a kidney-shaped placeholder 10 according to the invention, in comparison to a cuboid placeholder 10 according to the invention, is to be brought substantially more easily via an arcuate implantation path 70 to its site of action.

The method of implanting the placeholder 10 via the arcuate or straight implantation path 70 has already been described above.

Finally, it should be pointed out in particular, that the embodiments discussed above serve merely to describe the claimed teaching, but do not limit these to the embodiments. In particular, the embodiments described above—as far as possible—could be combined with one another. The multiplicity of the embodiments of the placeholder 10 according to the invention shown here shows a selection of the use of the features according to the invention alone as well as in combination: As has been shown here, each feature alone already achieves the object of the present invention. An additional benefit then arises once again from the combination of the features according to the invention.

The invention claimed is:

1. A placeholder for spinal surgery, comprising:
   an upper support having an upper support surface and a lower support having a lower support surface, a relative position of the upper support and the lower support being changeable, wherein the upper as well as the lower support surface each have a first sub-surface and a second sub-surface, which touch at edges thereof when the placeholder is in a closed state and
   an expansion device, by application of which the upper support surface and the lower support surface are each variable in lateral extension by a lateral moving apart of the first subsurface and second sub-surface of each of the upper support surface and the lower support surface up to a maximum separation amount between a minimum lateral extension and a maximum lateral extension as well as in a vertical distance between a minimum height and a maximum height of the placeholder, so that the placeholder can be adjusted between a closed and an expanded state;
   the expansion device being located between the upper support surface and the lower support surface, the first subsurface and second sub-surface of each of the upper support and the lower support having a perimeter and the expansion device being enclosed within the perimeter in both the closed state and the expanded state; and
   wherein the expansion device is configured to carry out the change in the lateral extension and the vertical distance in two movement courses which are independent of one another and freely definable and structurally coded in the placeholder, by operation of a single drive.

2. The placeholder for spinal surgery according to claim 1, wherein:
   the first sub-surface and the second sub-surface of the upper support as well as the first sub-surface and the second sub-surface of the lower support surface comprise an interengaging structure on the edges at which they touch in the closed state, which is designed such that, in the event of an expansion, the interengaging structure permits a lateral moving apart of the first sub-surface as well as the second sub-surface and, in the expanded state, a lateral gap running perpendicular to the direction of the lateral moving apart through the upper and the lower support surface has a gap width, which is smaller than the maximum separation amount.

3. The placeholder according to claim 2, wherein the gap width of the lateral gap is zero even in the expanded state.

4. The placeholder according to claim 2, wherein the upper and the lower support are shaped in such a way that, during the lateral moving apart, the interengaging structure of the first sub-surface slides mounted on a first support structure in a part of the support associated with the second sub-surface and the interengaging structure of the second sub-surface slides mounted on a second support structure in a part of the support associated with the first sub-surface.

5. The placeholder according to claim 2, wherein the expansion device for setting the placeholder between the closed and the expanded state includes a screw spindle with a screw head, by operation of which the change in the lateral extension as well as the vertical distance is controlled.

6. The placeholder according to claim 5, which has no symmetries along an axis, which runs parallel to the axis of the screw spindle, in any lateral cross section.

7. The placeholder according to claim 5, the expansion device of which further comprises a movable spacer element,
   wherein the movable spacer element is mounted so as to be laterally translatable along a movable axis and about a rotatable screw spindle that the movable spacer element is displaced along by operation of a threaded nut which is located concentric with the movable axis and runs on a thread of the screw spindle, wherein the movable axis is arranged running directly or indirectly in an upper elongated hole in the first sub-surface of the upper support and in a lower elongated hole in the first sub-surface of the lower support,
   wherein the movable spacer element is further laterally rotatable about a fixed axis, which is mounted in the second sub-surface of the upper support and in the second sub-surface of the lower support in a laterally positionally invariable manner, and
   wherein the movable spacer element is mounted on a first end and/or a second end in a freely sliding manner on an upper three-dimensional sliding surface below the first sub-surface and/or the second sub-surface of the upper support and on a lower three-dimensional sliding surface above the first sub-surface and/or the second sub-surface of the lower support, wherein the upper three-dimensional sliding surface and the lower three-dimensional sliding surface are shaped with respect to one another such that the first end and/or second end of the spacer element assumes a defined position on the upper three-dimensional sliding surface as well as on the lower three-dimensional sliding surface for each angle of rotation of the spacer element about the fixed axis, a location of which and the corresponding position of the movable axis in the correspondingly shaped elongated holes determines the lateral extension of the placeholder and the distance of which between the upper and the lower three-dimensional sliding surface from each other in the closed state determines the height of the placeholder.

8. The placeholder according to claim 5, wherein the expansion device further comprises a movable spacer element,
   wherein the movable spacer element can be moved along the screw spindle and has four guide elements, which are in each case displaceable in a first upper elongated hole and/or below a first upper guide sliding surface in the first sub-surface and in a second upper elongated hole and/or below a second upper guide sliding surface of the second sub-surface of the upper support and in a first lower elongated hole and/or on a first lower guide sliding surface of the first sub-surface and in a second lower elongated hole and/or on a second lower guide sliding surface of the second sub-surface of the lower support,
   wherein the spacer element comprises upper and lower, three-dimensional, sliding surfaces, and
   wherein the upper sliding surface and the lower sliding surface on the spacer element are shaped in respect to one another, and the elongated holes and/or guide sliding surfaces are shaped and arranged in each of the first sub surface and second sub-surface of the upper and lower supports in such a way that, for a defined position, which the spacer element assumes on the screw spindle, the corresponding position of the guide elements in the correspondingly shaped elongated holes and/or guide sliding surfaces determines the lateral extension of the placeholder and the distance of which between the upper sliding surface and lower sliding surface from one another on the spacer element at a touching edge and/or at a position of the upper and lower guide sliding surfaces of the upper and of the lower support, associated with the position of the spacer element, determines the height of the placeholder.

9. The placeholder according to claim 8, wherein the screw spindle comprises a thread on a second half, which runs in the opposite direction to a thread on a first half of the screw spindle, and the expansion device comprises a first spacer element or a first double pair of spacer elements, which use(s) the first half of the screw spindle, and a second spacer element or a second double pair of spacer elements, which uses the second half of the screw spindle, wherein first or second upper and lower three-dimensional sliding surfaces and corresponding upper and lower elongated holes and/or guide sliding surfaces are associated with first and second spacer element or double pair of spacer elements.

10. The placeholder according to claim 9, wherein the screw spindle comprises a guide structure between the first half and the second half and/or between the first spacer element and the second spacer element or the first double pair of spacer elements and the second double pair of spacer elements, which is mounted in a retaining element to be rotatable but laterally not displaceable in position, wherein the retaining element is mounted movably, but in turn is laterally not displaceable in its position in the upper support and in the lower support.

11. The placeholder according to claim 8, having a first spacer element and a second spacer element or a first double pair of spacer elements and a second double pair of spacer elements, wherein the first spacer element and the second spacer element or the first double pair of spacer elements and the second double pair of spacer elements are designed and arranged working in a mirror-imaged manner with respect to one another, or wherein the first spacer element and the second spacer element or the first double pair of spacer elements and the second double pair of spacer elements are designed and arranged working in same directions.

12. The placeholder according to claim 8, wherein a shape and a position of the three-dimensional sliding surfaces and a shape and a position of the elongated hole and/or the guide sliding surfaces are designed according to an individually required expansion behaviour.

13. The placeholder according to claim 5, wherein the expansion device further comprises a movable double pair of spacer elements,
   which in a position of each spacer element of the double pair in each case is mounted in a laterally rotatable manner about a movable axis, wherein the movable axes are arranged on a threaded nut, and are displaceable along the screw spindle by operation of the threaded nut running on a thread of the screw spindle,
   wherein the first spacer element of the double pair is laterally rotatable about a fixed axis, which is mounted in the first sub-surface of the upper support and in the first sub-surface of the lower support in a laterally positionally invariable manner, and the second spacer element of the double pair is laterally rotatable about a fixed axis, which is mounted in the second sub-surface of the upper support and in the second sub-surface of the lower support in a laterally positionally invariable manner, and wherein the threaded nut running on the thread of the screw spindle is designed such that it comprises sliding surfaces or a double toggle lever structure for the first sub-surface and second sub-surface of the upper support and for the first sub-surface and second sub-surface of the lower support, which are mounted in a freely sliding manner on guide sliding surfaces of the first sub-surface and second sub-surface of the upper support and on guide sliding surfaces of the first sub-surface and second sub-surfaces of the lower support, and wherein an angular position between the first spacer element and the second spacer element determines the lateral extension of the placeholder and a distance of the upper and lower sliding surface relative to one another or a position of the double toggle lever structure at a touching edge and/or at a position of the upper guide sliding surface and lower guide sliding surface of the upper support and of the lower support associated with the position of the threaded nut determines the height of the placeholder.

14. The placeholder according to claim 2, wherein in a top view, the placeholder has a kidney-shaped form.

15. The placeholder according to claim 2, having a minimum height of greater than or equal to 7 mm in the closed state and a maximum height of less than or equal to 14 mm in the expanded state and a lateral extension of greater than or equal to 13 mm in the closed state.

16. The placeholder according to claim 1, wherein the expansion device for setting the placeholder between the closed and the expanded state includes a screw spindle with a screw head, by operation of which the change in the lateral extension as well as the vertical distance is controlled.

17. The placeholder according to claim 16, which has no symmetries along an axis, which runs parallel to the axis of the screw spindle, in any lateral cross section.

18. The placeholder according to claim 16, the expansion device of which further comprises a movable spacer element, wherein the movable spacer element is mounted so as to be laterally translatable along a movable axis and about a rotatable screw spindle that the movable spacer element is displaced along by operation of a threaded nut which is located concentric with the movable axis and runs on a thread of the screw spindle, wherein the movable axis is arranged running directly or indirectly in an upper elongated hole in the first sub-surface of the upper support and in a lower elongated hole in the first sub-surface of the lower support, wherein the movable spacer element is further laterally rotatable about a fixed axis, which is mounted in the second sub-surface of the upper support and in the second sub-surface of the lower support in a laterally positionally invariable manner, and wherein the movable spacer element is mounted on a first end and/or a second end in a freely sliding manner on an upper three-dimensional sliding surface below the first sub-surface and/or the second sub-surface of the upper support and on a lower three-dimensional sliding surface above the first sub-surface and/or the second sub-surface of the lower support, wherein the upper three-dimensional sliding surface and the lower three-dimensional sliding surface are shaped with respect to one another such that the first end and/or second end of the spacer element assumes a defined position on the upper three-dimensional sliding surface as well as on the lower three-dimensional sliding surface for each angle of rotation of the spacer element about the fixed axis, a location of which and the corresponding position of the movable axis in the correspondingly shaped elongated holes determines the lateral extension of the placeholder and the distance of which between the upper and the lower three-dimensional sliding surface from each other in the closed state determines the height of the placeholder.

19. The placeholder according to claim 16, wherein the expansion device further comprises a movable spacer element, wherein the movable spacer element can be moved along the screw spindle and has four guide elements, which are in each case displaceable in a first upper elongated hole and/or below a first upper guide sliding surface in the first sub-surface and in a second upper elongated hole and/or below a second upper guide sliding surface of the second sub-surface of the upper support and in a first lower elongated hole and/or on a first lower guide sliding surface of the first sub-surface and in a second lower elongated hole and/or on a second lower guide sliding surface of the second sub-surface of the lower support, wherein the spacer element comprises upper and lower, three-dimensional, sliding surfaces, and wherein the upper sliding surface and the lower sliding surface on the spacer element are shaped in respect to one another, and the elongated holes and/or guide sliding surfaces are shaped and arranged in each of the first sub surface and second sub-surface of the upper and lower supports in such a way that, for a defined position, which the spacer element assumes on the screw spindle, the corresponding position of the guide elements in the correspondingly shaped elongated holes and/or guide sliding surfaces determines the lateral extension of the placeholder and the distance of which between the upper sliding surface and lower sliding surface from one another on the spacer element at a touching edge and/or at a position of the upper and lower guide sliding surfaces of the upper and of the lower support, associated with the position of the spacer element, determines the height of the placeholder.

20. The placeholder according to claim 19, wherein the screw spindle comprises a thread on a second half, which runs in the opposite direction to a thread on a first half of the screw spindle, and the expansion device comprises a first spacer element or a first double pair of spacer elements, which use(s) the first half of the screw spindle, and a second spacer element or a second double pair of spacer elements, which uses the second half of the screw spindle, wherein first or second upper and lower three-dimensional sliding surfaces and corresponding upper and lower elongated holes and/or guide sliding surfaces are associated with first and second spacer element or double pair of spacer elements.

21. The placeholder according to claim 20, wherein the screw spindle comprises a guide structure between the first half and the second half and/or between the first spacer element and the second spacer element or the first double pair of spacer elements and the second double pair of spacer elements, which is mounted in a retaining element to be rotatable but laterally not displaceable in position, wherein the retaining element is mounted movably, but in turn is laterally not displaceable in its position in the upper support and in the lower support.

22. The placeholder according to claim 19, having a first spacer element and a second spacer element or a first double pair of spacer elements and a second double pair of spacer elements, wherein the first spacer element and the second spacer element or the first double pair of spacer elements and the second double pair of spacer elements are designed and arranged working in a mirror-imaged manner with respect to one another, or wherein the first spacer element and the second spacer element or the first double pair of spacer elements and the second double pair of spacer elements are designed and arranged working in same directions.

23. The placeholder according to claim 19, wherein a shape and a position of the three-dimensional sliding surfaces and a shape and a position of the elongated hole and/or the guide sliding surfaces are designed according to an individually required expansion behaviour.

24. The placeholder according to claim 16, wherein the expansion device further comprises a movable double pair of spacer elements,
which in a position of each spacer element of the double pair in each case the spacer element is mounted in a laterally rotatable manner about a movable axis, wherein the movable axes are arranged on a threaded nut, and are displaceable along the screw spindle by operation of the threaded nut running on a thread of the screw spindle,
wherein the first spacer element of the double pair is laterally rotatable about a fixed axis, which is mounted in the first sub-surface of the upper support and in the first sub-surface of the lower support in a laterally positionally invariable manner, and the second spacer element of the double pair is laterally rotatable about a fixed axis, which is mounted in the second sub-surface of the upper support and in the second sub-surface of the lower support in a laterally positionally invariable manner, and
wherein the threaded nut running on the thread of the screw spindle is designed such that it comprises sliding surfaces or a double toggle lever structure for the first sub-surface and second sub-surface of the upper support and for the first sub-surface and second sub-surface of the lower support, which are mounted in a freely sliding manner on guide sliding surfaces of the first sub-surface and second sub-surface of the upper support and on guide sliding surfaces of the first sub-surface and second sub-surfaces of the lower support,
and wherein an angular position between the first spacer element and the second spacer element determines the lateral extension of the placeholder and a distance of the upper and lower sliding surface relative to one another or a position of the double toggle lever structure at a touching edge and/or at a position of the upper guide sliding surface and lower guide sliding surface of the upper support and of the lower support associated with the position of the threaded nut) determines the height of the placeholder.

25. The placeholder according to claim 1, wherein in a top view, the placeholder has a kidney-shaped form.

26. The placeholder according to claim 1, having a minimum height of greater than or equal to 7 mm in the closed state and a maximum height of less than or equal to 14 mm in the expanded state and a lateral extension of greater than or equal to 13 mm in the closed state.

* * * * *

UNITED STATES PATENT AND TRADEMARK OFFICE
CERTIFICATE OF CORRECTION

PATENT NO. : 11,737,886 B2
APPLICATION NO. : 17/051619
DATED : August 29, 2023
INVENTOR(S) : Bernhard Rieger It is certified that error appears in the above-identified patent and that said Letters Patent is hereby corrected as shown below:

On the Title Page

In Item (71), under "Applicant", in Column 1, Line 1, delete "Frechen, DE (US)" and insert --Frechen (DE)--

In Item (57), under "ABSTRACT", in Column 2, Line 1, delete "place holder" and insert --placeholder--

In Item (57), under "ABSTRACT", in Column 2, Line 2, delete "which" and insert --in which--

In Item (57), under "ABSTRACT", in Column 2, Lines 6-7, delete "place holder" and insert --placeholder--

In Item (57), under "ABSTRACT", in Column 2, Lines 14-15, delete "place holder." and insert --placeholder.--

Page 2 In Item (56), under "OTHER PUBLICATIONS", in Column 1, Line 2, delete "PCTZEP2019/060834" and insert --PCT/EP2019/060834--

In the Specification

Column 6, Line 62, delete "di stance." and insert --distance.--

Column 7, Line 62, delete "by a" and insert --by--

Column 8, Line 58, delete "wave form" and insert --waveform--

Column 11, Line 45, delete "middle in" and insert --middle of--

Column 15, Line 29, delete "these" and insert --this--

Signed and Sealed this
Thirteenth Day of February, 2024

Katherine Kelly Vidal
*Director of the United States Patent and Trademark Office*

CERTIFICATE OF CORRECTION (continued)
U.S. Pat. No. 11,737,886 B2

Column 15, Line 56, delete "(facetotomy)," and insert --(facetectomy),--

Column 16, Line 42, delete "(by means" and insert --by means--

Column 16, Line 42, delete "facetotomy" and insert --facetectomy--

Column 17, Line 53, delete "an vertebral" and insert --a vertebral--

Column 21, Line 37, delete "expanded" and insert --expanded by--

Column 22, Line 54, delete "FIG. 10 an" and insert --FIG. 10 depicts an--

Column 23, Line 36, delete "displaceably," and insert --displaceable,--

Column 24, Line 20, delete "displaceably" and insert --displaceable--

Column 25, Line 26, delete "in in" and insert --in--

Column 27, Lines 38-39, delete "there through." and insert --therethrough.--

In the Claims

Column 28, Line 17, in Claim 1, delete "state and" and insert --state;--

Column 28, Line 35, in Claim 1, delete "and" and insert the same on Line 34, after "expanded state;"

Column 31, Line 3, in Claim 13, delete "manner, and" and insert --manner,--

Column 31, Line 15, in Claim 13, delete "and" and insert the same on Lines 13-14, after "support,"

Column 34, Line 5, in Claim 24, delete "manner, and" and insert --manner,--

Column 34, Line 17, in Claim 24, delete "and" and insert the same on Lines 15-16, after "support,"

Column 34, Line 25, in Claim 24, delete "nut)" and insert --nut--